(12) United States Patent
Allinson

(10) Patent No.: US 8,712,586 B2
(45) Date of Patent: Apr. 29, 2014

(54) DISPENSING OF RESTRICTED GOODS

(75) Inventor: John Clive Allinson, Balwyn North (AU)

(73) Assignee: Bluepoint International Pty Ltd, Victoria (AU)

( * ) Notice: Subject to any disclaimer, the term of this patent is extended or adjusted under 35 U.S.C. 154(b) by 189 days.

(21) Appl. No.: 13/315,330

(22) Filed: Dec. 9, 2011

(65) Prior Publication Data

US 2012/0232693 A1  Sep. 13, 2012

Related U.S. Application Data

(63) Continuation-in-part of application No. 12/089,461, filed as application No. PCT/AU2006/001458 on Oct. 6, 2006, now Pat. No. 8,078,317.

(51) Int. Cl.
*G06F 17/00* (2006.01)

(52) U.S. Cl.
USPC ........... 700/242; 700/236; 700/240; 700/237; 221/97; 221/133

(58) Field of Classification Search
USPC ............. 221/97, 133; 700/236, 237, 240, 244
See application file for complete search history.

(56) References Cited

U.S. PATENT DOCUMENTS

| | | | |
|---|---|---|---|
| 4,845,636 A | 7/1989 | Walker | |
| 6,529,801 B1 | 3/2003 | Rosenblum | |
| 6,711,460 B1 | 3/2004 | Reese | |
| 6,735,497 B2 | 5/2004 | Wallace et al. | |
| 6,742,671 B2 * | 6/2004 | Hebron et al. | 221/9 |
| 6,766,218 B2 | 7/2004 | Rosenblum | |
| 6,892,941 B2 | 5/2005 | Rosenblum | |
| 7,006,893 B2 | 2/2006 | Hart et al. | |
| 7,080,755 B2 | 7/2006 | Handfield et al. | |
| 7,123,989 B2 | 10/2006 | Pinney et al. | |
| 7,151,982 B2 | 12/2006 | Liff et al. | |
| 7,344,047 B2 | 3/2008 | Gilmore | |
| 7,344,050 B2 * | 3/2008 | Robrechts | 221/120 |
| 7,474,938 B2 * | 1/2009 | Poliner | 700/242 |
| 7,630,788 B1 * | 12/2009 | Reese | 700/237 |
| 7,721,914 B2 | 5/2010 | Handfield et al. | |
| 7,735,681 B2 | 6/2010 | Handfeld et al. | |
| 7,774,097 B2 | 8/2010 | Rosenblum | |
| 7,783,378 B2 | 8/2010 | Pinney et al. | |
| 7,783,379 B2 | 8/2010 | Beane et al. | |
| 7,787,986 B2 * | 8/2010 | Pinney et al. | 700/232 |
| 8,078,317 B2 * | 12/2011 | Allinson et al. | 700/237 |
| 2005/0023286 A1 | 2/2005 | Pinney et al. | |

FOREIGN PATENT DOCUMENTS

| | | |
|---|---|---|
| AU | 2003/203618 A1 | 1/2004 |
| AU | 2004/101011 A4 | 1/2005 |
| WO | WO-2006/070359 A2 | 7/2006 |

\* cited by examiner

*Primary Examiner* — Timothy Waggoner
(74) *Attorney, Agent, or Firm* — Novak Druce Connolly Bove + Quigg LLP

(57) ABSTRACT

A method of dispensing restricted products includes providing: a dispenser containing an inventory of restricted goods and a communication link to an authorized vendor; means to enable the vendor to verify the purchaser as an approved purchaser; an inventory system including storage for products in rows and columns; an identification system that identifies the location of each product by row and column; a product section device enabling verification that the selected product is correct and moves the product to a printing location, a viewing location, and/or an issue tray; a visual viewing means for the vendor to view the product; a payment transaction system to verify payment for the product; at least two collection trays remaining locked until the vendor releases product to the purchaser; a product reject hopper to collect product not approved for collection; and reject system to securely remove product to the reject hopper.

6 Claims, 20 Drawing Sheets

DISPENSING OF RESTRICTED GOODS

PRIORITY

Priority is claimed as a continuation-in-part application to U.S. patent application Ser. No. 12/089,461, filed Apr. 7, 2008, which claims priority as a national stage application to PCT/AU2006/001458, filed Oct. 6, 2006, which claims priority to Australian Patent Application No. 2005/905515, filed on Oct. 7, 2005. The disclosures of the aforementioned priority applications are incorporated herein by reference in their entirety.

FIELD OF THE INVENTION

This invention relates to the vending and dispensing of goods that have government regulations controlling their sale and in particular is concerned with dispensing ethical pharmaceuticals that normally require a prescription from a physician.

BACKGROUND TO THE INVENTION

The problem of providing remote and after hours supply of pharmaceuticals has been addressed before.

U.S. Pat. Nos. 6,330,491 and 6,438,451 disclose a system for automating the dispensing of drugs using a dispensing machine. The script is sent over the internet from the doctors premises or the patient's premises and the drugs are made available at the dispensing machine by the pharmacist. No direct contact between the patient and the pharmacist occurs.

U.S. Pat. Nos. 6,564,121 and 6,735,497 provide an internet based system of communicating a script to a pharmacy which then makes the drugs available by mail or at a designated pick up point which may be a dispensing machine. Again there is no contact between the patient and pharmacist.

U.S. Pat. No. 6,871,783 discloses a pharmacy remote link for scanning and sending script to Pharmacy and also for payment. There is no disclosure of a dispensing machine.

U.S. Pat. Nos. 6,529,801 and 6,766,218 disclose a similar arrangement in that a script is sent by a doctor to a pharmacist for delivery from a vending machine. The vending machine includes a gantry row and column product transport system with magazines of product and uses a pusher to move product from each product magazine onto the gantry carrier. The gantry carrier has a bar code scanner to identify the contents of each magazine. The machine includes a reject bin if the bar code scan is not positive. The dispenser needs an authorization code to actuate the dispensing of the drugs.

These prior art attempts at dealing with this problem depend on the doctor or patient sending the prescription electronically to the pharmacist whereas often the patient has a hard copy of the prescription and may not be able to send this to the pharmacist. The dispensing machines do not allow any interaction by the consumer with the pharmacist and this is usually unsatisfactory for the consumer and in some jurisdictions does not comply with the regulations.

Australian patent application 2003203618 discloses a pharmaceutical dispenser communicating with a remote pharmacist. The dispenser has a video that can scan one of prescription or purchaser and incorporates a printer to print a label. The dispenser can be actuated by the pharmacist to release the package. This disclosure goes part of the way in improving the control and quality of remote dispensing.

It is an object of this invention to provide a remote dispensing machine for pharmaceuticals or other restricted goods that allows for direct communication between the purchaser and the vendor in a manner that is convenient and fail safe.

BRIEF DESCRIPTION OF THE INVENTION

To this end the present invention provides a method of dispensing restricted products from an authorized vendor to an approved purchaser which includes the steps of
a) providing a dispenser containing an inventory of restricted goods
b) providing an audio communication and optionally a data link from the dispenser to the authorized vendor
c) providing means in the dispenser to enable the vendor to verify the purchaser's status as an approved purchaser
d) providing an inventory system that includes product storage in rows and columns and a product identification system that identifies the location of each storage location and product by its row and column
e) providing a product selection device that verifies that the product selected is correct and holds and carries the product from its storage location to one or more of a printing location, viewing location and issue tray all located within the dispenser
f) optionally providing a printing location to enable the product to be labeled
g) providing visual viewing means for the vendor to view the product before it is placed in the issue tray
h) providing a payment transaction system in the dispenser to verify payment for the product
i) providing an issue tray in the dispenser that is locked until the vendor releases the product to the purchaser
j) the dispenser including a reject system that securely removes product to a reject hopper at any time after the product is held by the product selection device but prior to the vendor releasing the product from the issue tray.

This method overcomes the short comings of the prior art by providing in the dispenser at least an audio link to enable the vendor and the purchaser to ask questions and ensure that each party to the transaction is satisfied and ensure compliance with the safety aspirations of the regulations. The vendor is additionally able to view and verify that the product is as specified and is able to abort the transaction if required.

The method may also include the steps of
a) providing a connection to a management server
b) providing a means in management server for identifying approved vendors
c) providing a means to manage authorised users, user locations, dispensing terminals, and the relationship between authorised vendors and dispensing terminals Throughout this specification the following terms have the meanings as set out below:

Restricted goods: means goods that require a licensed vendor and an authorization or licence to purchase or proof of age and includes pharmaceuticals, medical products, alcohol, cigarettes and firearms.

Authorised vendor: means a person licensed or approved to sell restricted goods and includes pharmacists, doctors, health professionals, holders of liquor licenses, managers of gambling and wagering establishments and firearms and explosives dealers and persons who can carry out some of these tasks on behalf of the licensed person.

Authorized purchaser: means anyone who can pass the age qualification or possess an authorisation to purchase such as a physician's prescription or a gun licence.

Payment transaction system; means any means to conclude the exchange of goods for consideration and includes a cash receiving system, electronic funds transfer, credit card transaction system, account debiting system, or any voucher or government agency authority such as the dispensing of pharmaceuticals to authorized persons free of charge.

The method is able to cope with several vendors and several dispensing machines. For example a pharmaceutical retailer may employ several registered pharmacists and have several dispensing machines at different locations. Any one of the pharmacists can respond to purchaser requests at any of the dispensers according to need.

The dispenser may be any secure device that can hold product and enable the purchaser to transact the purchase and collect the product.

In another aspect the present invention provides a dispenser for dispensing restricted goods by an authorized vendor to an approved purchaser which includes:
a) A cabinet containing an inventory storage system, a purchaser transaction module, a reject system and a control system
b) Said inventory storage system includes product storage in rows and columns
c) Said purchaser transaction module including an audio communication link from the dispenser to the authorized vendor, a payment transaction system in the dispenser to verify payment for the product and an issue tray in the dispenser that is locked until the vendor releases the product to the purchaser
d) Said reject system securely removes product to a reject hopper at any time after the product is held by the product selection device but prior to the vendor releasing the product from the issue tray.
e) Said control system including
   i) means to enable the vendor to verify the purchaser's status as an approved purchaser
   ii) a product identification system that identifies each storage location and stores the location of each product by its row and column
   iii) a product selection device that verifies that the product selected is correct and holds and carries the product from its storage location to one or more of a printing location, viewing location and issue tray all located within the dispenser
   iv) an optional printer to enable the product to be labeled
   v) an optional visual viewing means for the vendor to view the product before it is placed in the issue tray
   vi) actuation means to enable the vendor to actuate the reject system or unlock the issue tray.

The cabinet is intended to be a secure device akin to a financial automatic teller machine but in other respects similar to a product vending machine although the products are unlikely to be displayed to the purchaser until the transaction is completed.

Any suitable inventory storage system that uses a row and column system is suitable for this invention. Each row may consist of a shelf with a multiple set of compartments corresponding to the columns. Preferably the compartment widths are variable to accommodate various sizes of package and containers including packets and bottles. Thus each shelf may contain a different number of compartments (columns). The shelf spacing may also be varied so that all shelves are not necessarily equidistant. The arrangement of the compartment and shelf spacing is able to be identified by the controller or programmed in the controller so that the location of each storage location and product can be identified in the row and column configuration. The controller can recognize the position of each horizontal row and vertical column and also identify each product placed in each location. Identification is matched to a data base and confirmation that the correct product is in the correct chute location. If not the controller can pick and reject the product or follow a configurable command, to block picking from this location.

The purchaser transaction module may include input devices such as a keyboard, keypad and an audio link to a registered vendor. This enables the vendor and purchaser to converse and clarify any issues relating to the purchase and the use of the purchased product. In certain facilities the registered vendor would be able to access the transaction module and process the supply of a product on behalf of the purchaser.

Preferably, the module will also include a video camera to enable the vendor to view the purchaser and capture an image of the purchaser and the purchaser's identification document such as driver's licence or healthcare card which may establish identity and age as prerequisites for some transactions. The purchaser transaction module also preferably includes a scanner to scan any authorization documents such as a prescription from a physician or a gun licence. It is within the scope of this invention that the authorization documents may have previously been forwarded to the vendor or be available for viewing and retrieval on a network accessible database in which case the purchaser need only establish that they are the person to whom the authorization relates either by identification or use of an identification code or password. In some countries this is referred to as an electronic prescription (e-script). A unique ID may be provided on the paper copy of the script and scanned by the terminal using either a script scanner or laser scanner.

An essential component of the purchaser transaction module is the payment transaction system which may provide for the insertion of a credit or debit card and a personal identification number (PIN) and password or some other appropriate identification that enables the cost of the transaction to be debited against the account of the person or government agency responsible. The payment transaction may be completed after initiation of the transaction or at any time before the product is released from the collection or issue tray.

Based on the type of facility the payment module may not be necessary. Payment can be completed within existing processes in the dispensary point of sale. The system can output a coupon or receipt to record payment by other method if required.

The collection tray is a compartment in the dispenser into which the goods to be dispensed are transferred by the product selection system. It incorporates a lock that makes it inaccessible until the vendor actuates release. The collection tray also includes a reject mechanism that enables the issue tray to be emptied into a reject bin or for the products to be removed and placed in the reject receptacle should the transaction be aborted before the vendor actuates the release.

The reject system when actuated controls the product selection device so that it holds and carries the product to the reject receptacle. If the product selection device has already delivered the product to the collection tray when the reject system is actuated, it controls the collection tray to prevent it being unlocked until the products in the collection tray are removed to the reject bin. It is within the scope of this invention to incorporate more than one reject bin. One may be located in the processing module, a second one may be located below the collection tray and a third may be located in the inventory storage area.

The control system is primarily a programmable computer with a data storage system that is primarily accessed and controlled by the authorized vendor but is initiated by the purchaser beginning a transaction. The purchaser can only begin a transaction request if an authorised vendor is logged into the system and available for service. Once the product request is made the control system is programmed to search the inventory database to check if it is available. The product request may be made by the presentation of the purchase authorization such as a pharmaceutical prescription or by the vendor or purchaser keying in the product code or the purchaser verbally requesting the product and the vendor keying in the code. Once the product has been identified and its availability and location in the storage identified, the product selection system can be actuated. The product selection system is preferably a pick and place gantry system moving horizontally and vertically in accordance with the compartment and shelf locations of the storage system. The pick up unit incorporates a bar code reader or similar device such as a camera to verify that the bar code on the product in the compartment is the same as the bar code of the requested product or to enable the authorised vendor to confirm the product to be picked is correct. If it is correct the pick up unit carries carries the product to the camera location for identification and viewing by the authorised vendor. The camera location may provide several camera views of the product to ensure that all or several views of the product are able to be viewed by the authorised vendor to ensure that the product selected is correct. The camera location may also contain multiple machine identification devices such as barcode scanners or RFID receivers to ensure that the product selected and picked is correct. Once confirmation is provided by the authorised vendor, the product is then carried to the label printing station. If the product selected is incorrect then the unit conveys it to a chute that leads to the reject bin.

The pick up unit can use any pick and hold mechanism such as a suction grip for light packages or a robotic hand. The printing station is intended primarily for use with pharmaceuticals where it is conventional for the pharmacist to add a label specifying the quantity and timing of the administration of the pharmaceutical. It may also indicate the date the product was dispensed from the dispenser. The product selection device may then convey the product to a video camera location so that the vendor and optionally the purchaser can view the product to ensure it is correct. If at this point the authorized vendor decides the product is incorrect or incorrectly labeled the transaction may be aborted and the product selection unit conveys it directly to a chute that leads to the reject bin. If the vendor approves the product it is conveyed to the issue tray. When the payment transaction is completed the vendor actuates the unlocking of the issue tray so that the product can be collected by the purchaser. Any documentation, such as a receipt or a repeat prescription or authorization for another purchase, is preferably deposited in the issue tray although they could be issued through another slot in the purchaser module.

DETAILED DESCRIPTION OF THE INVENTION

A preferred embodiment of the invention which is a pharmaceutical retailing system and dispenser for pharmaceutical products will be described with reference to the drawings in which:

FIG. 1 provides a schematic representation of the pharmacy network system with a terminal remote dispensing machine (RDM);

Figure 8:
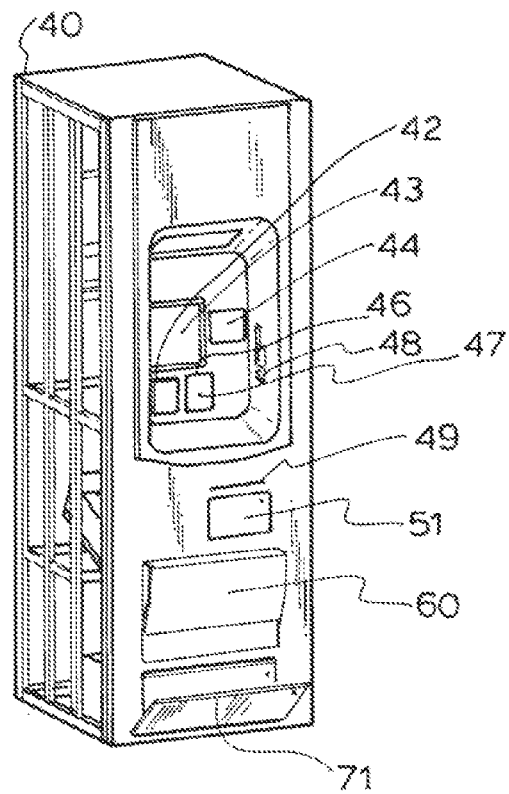
FIG. 8 is an external view of the purchaser interface module of the RDM.
Figure 11A:
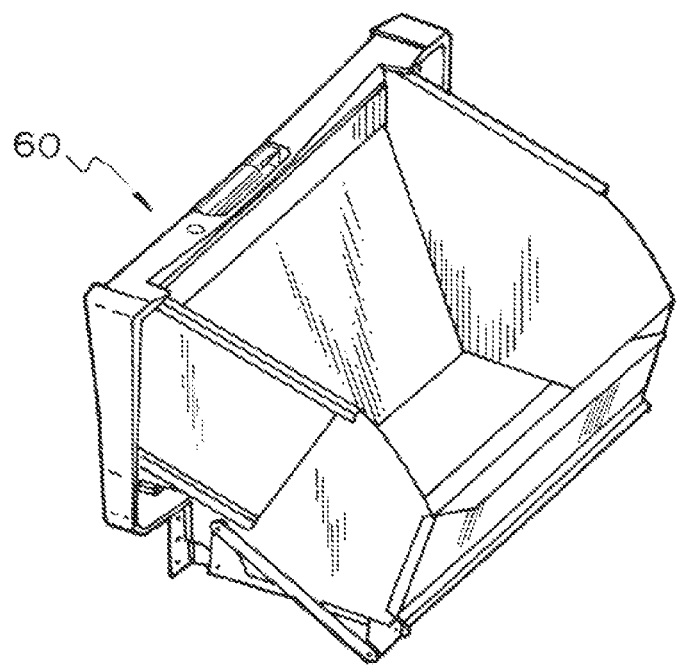
Figure 12A:
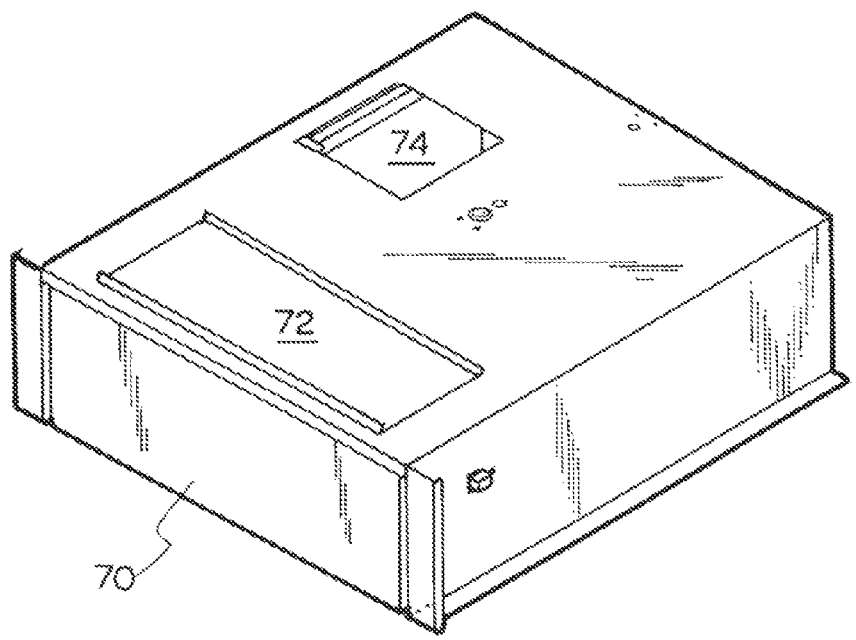
Figure 13A:
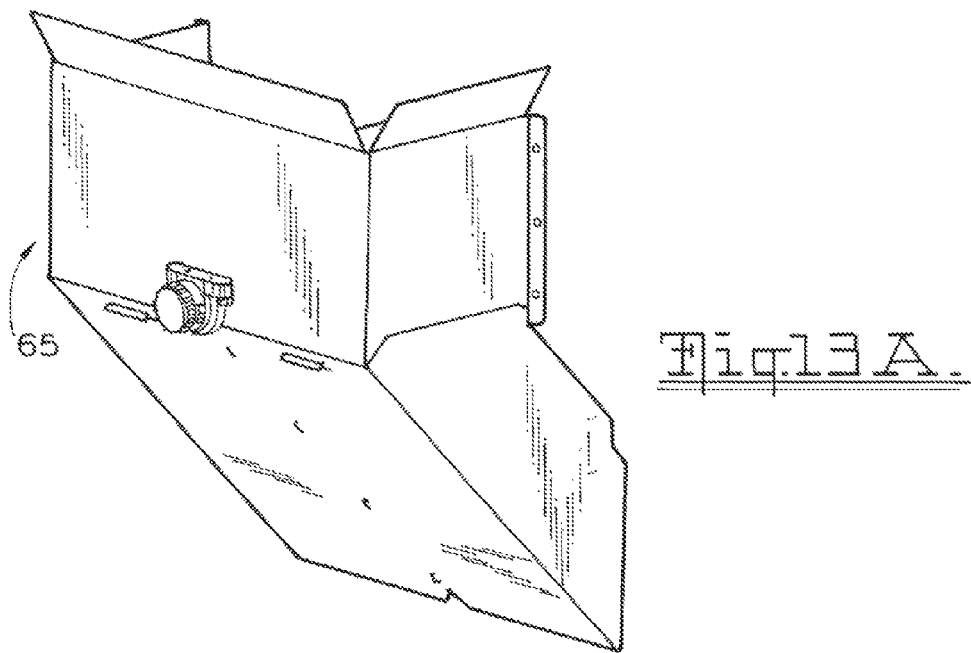
Figure 14:
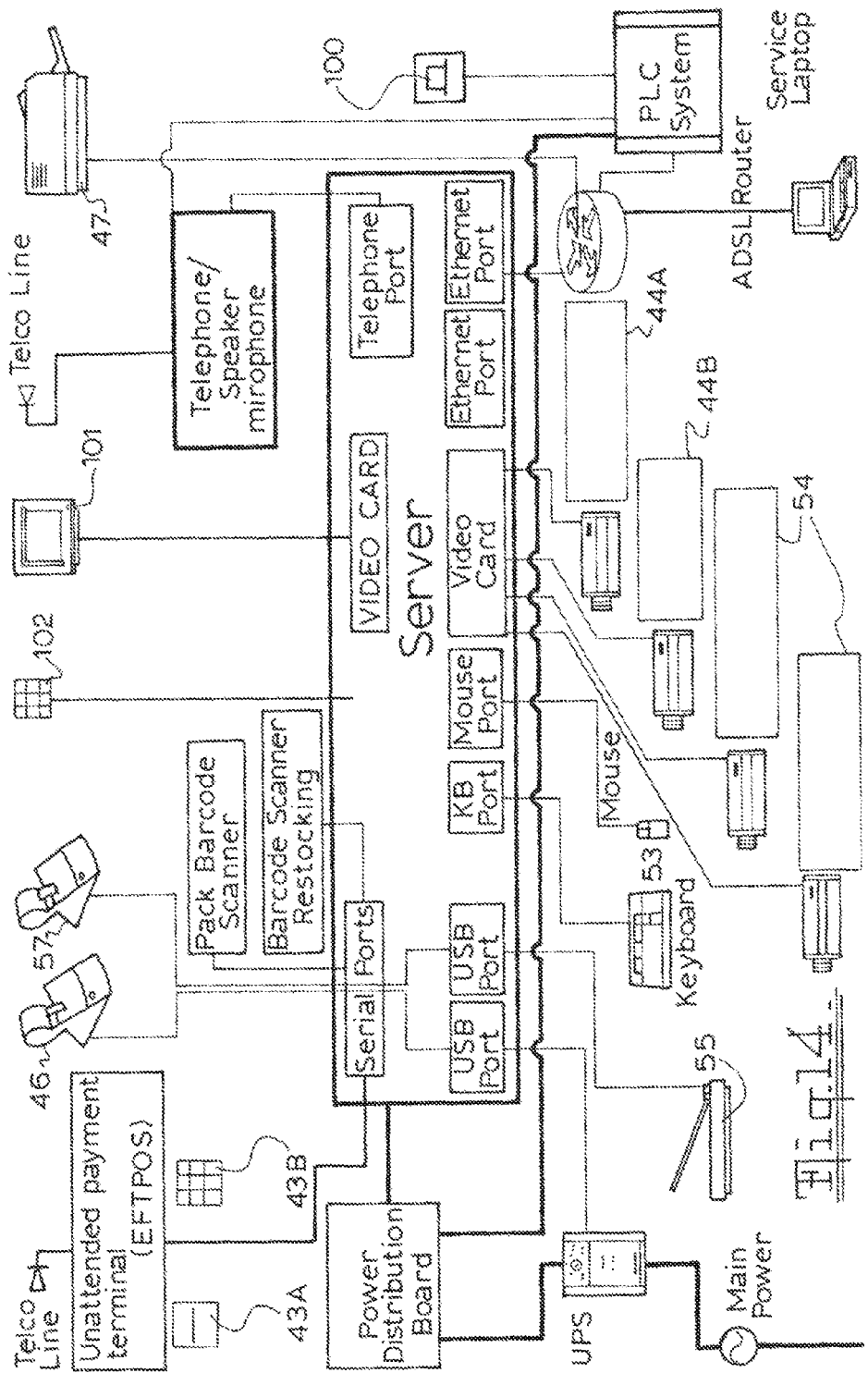
Figure 15:
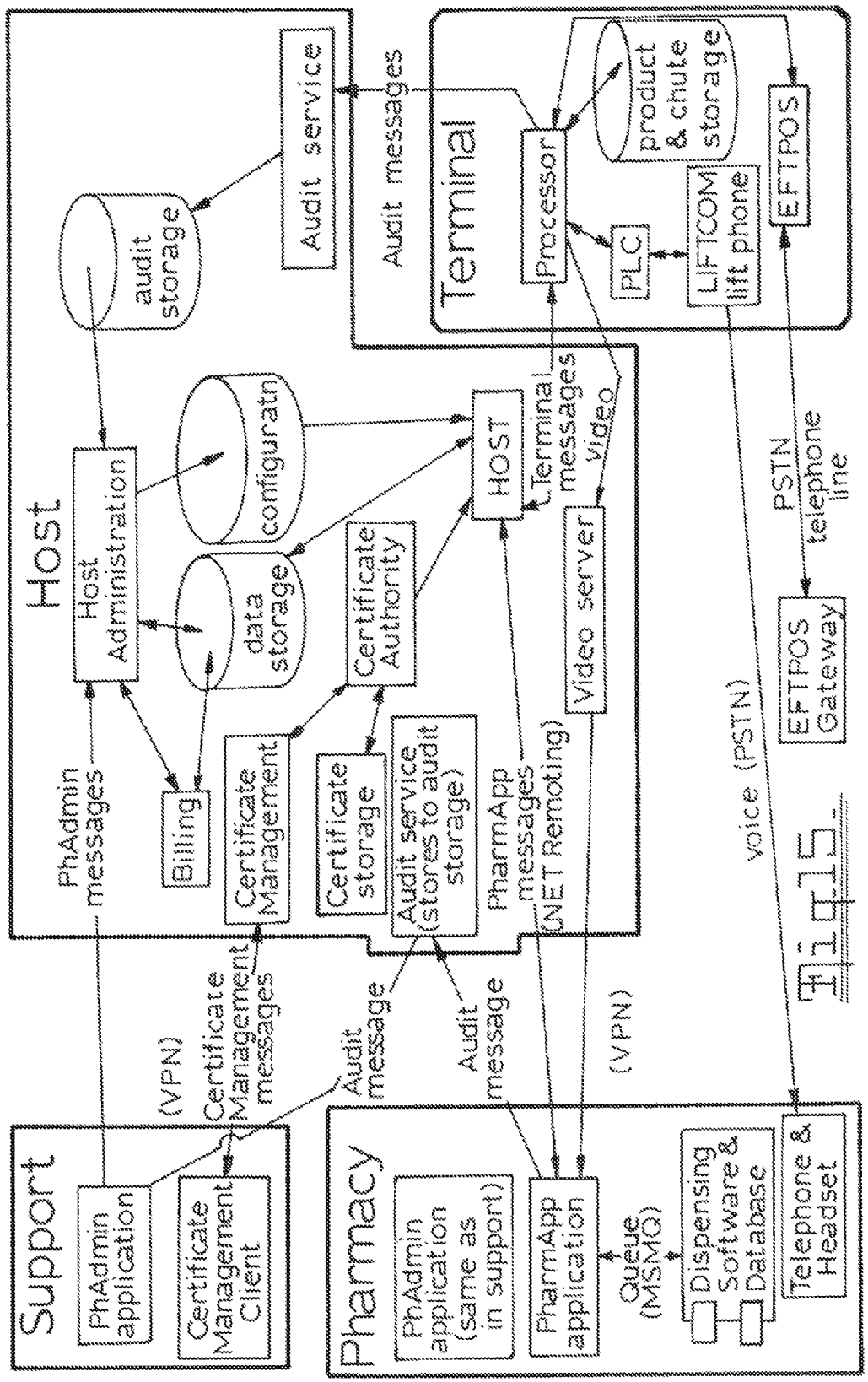
Figure 15:
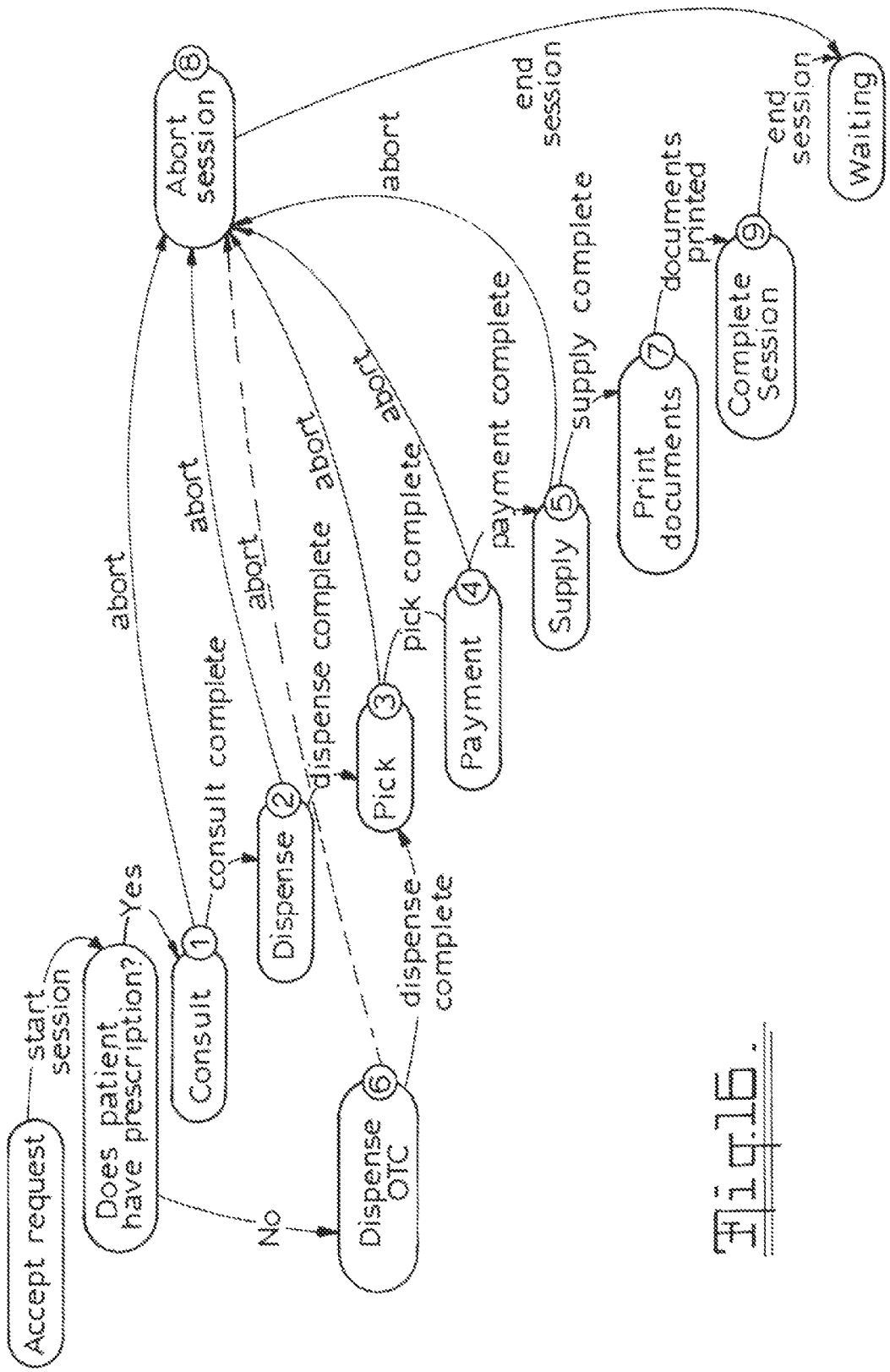
Figure 17:
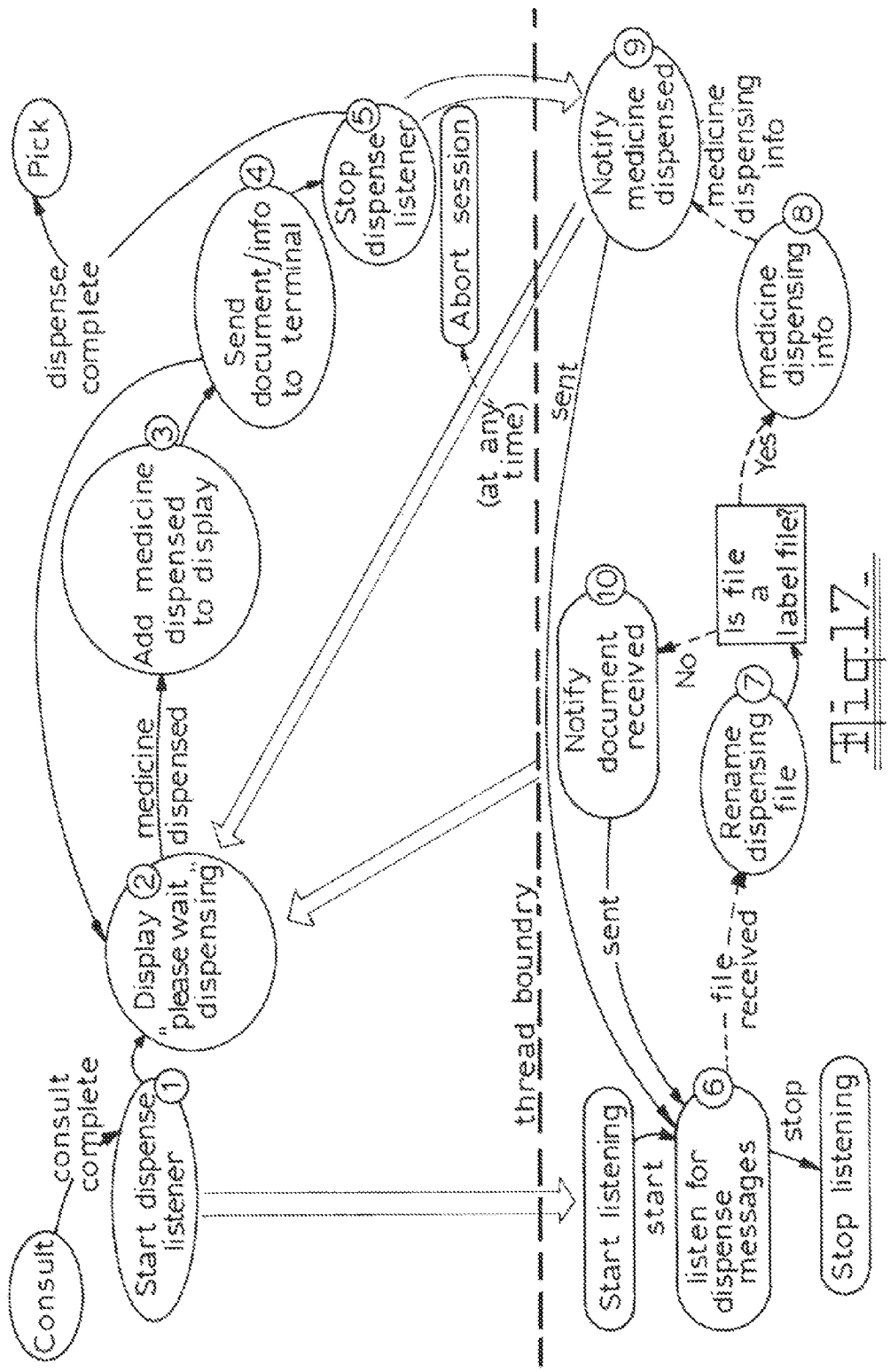
Figure 18:
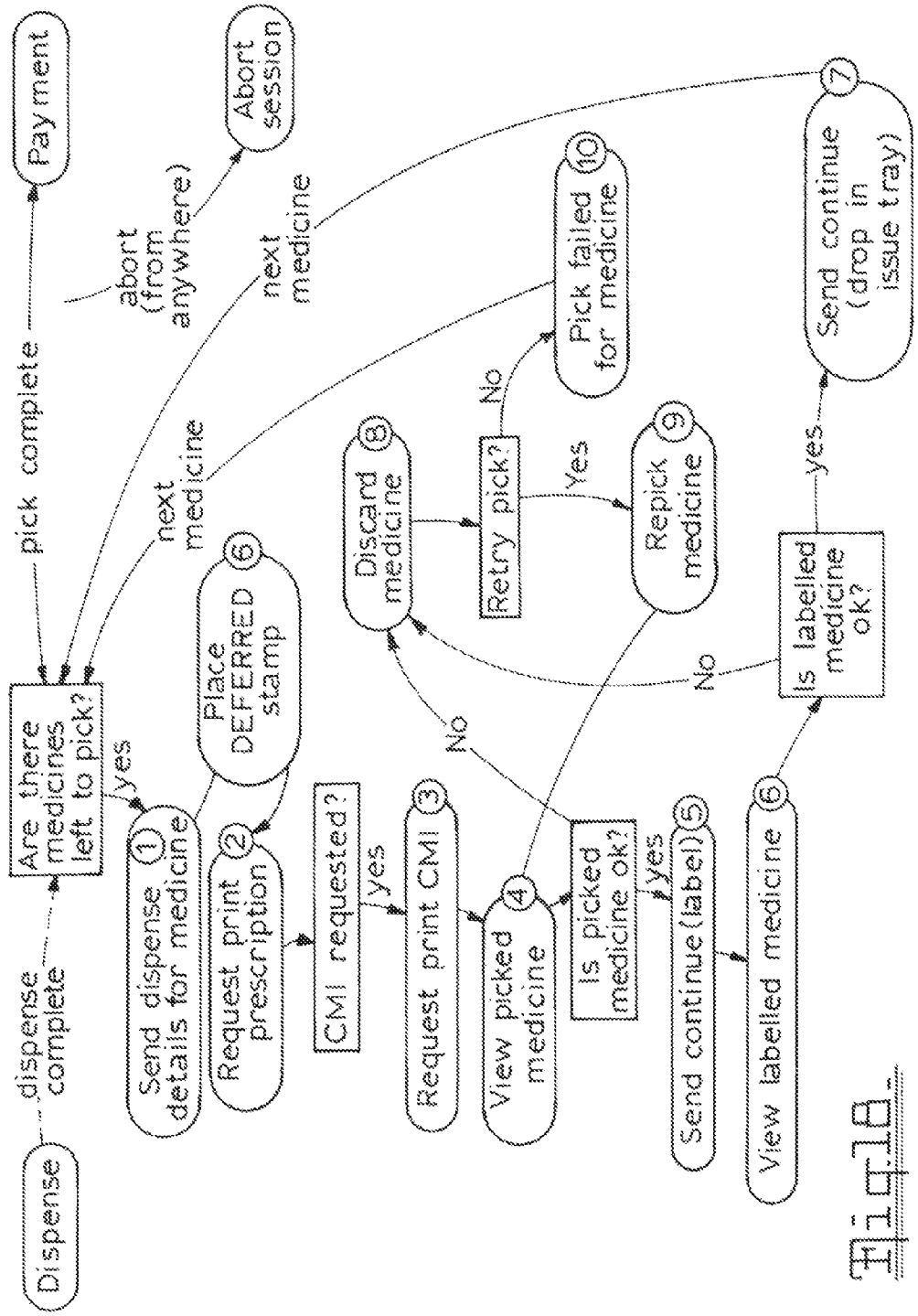
Figure 19:
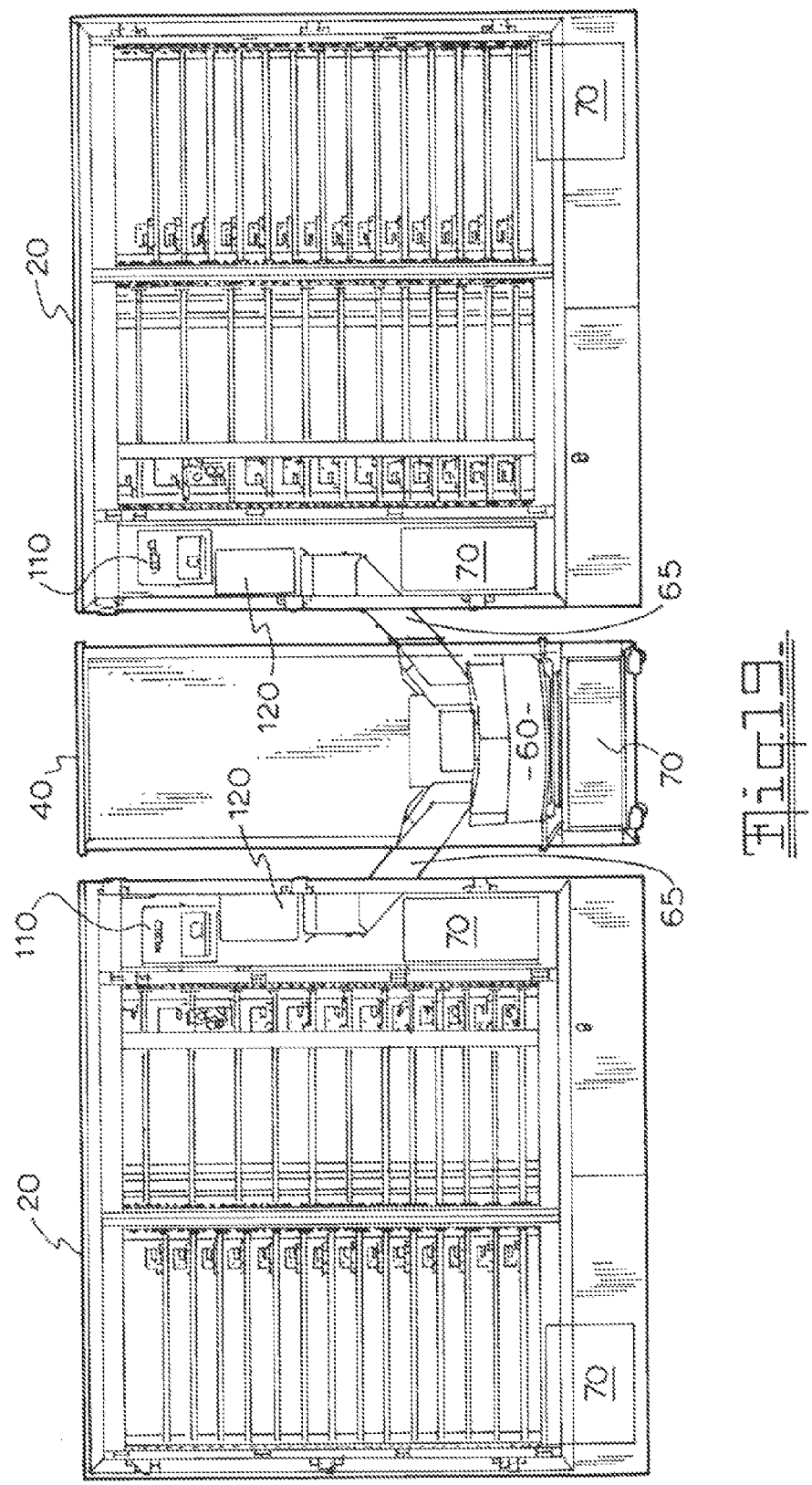
Figure 21:
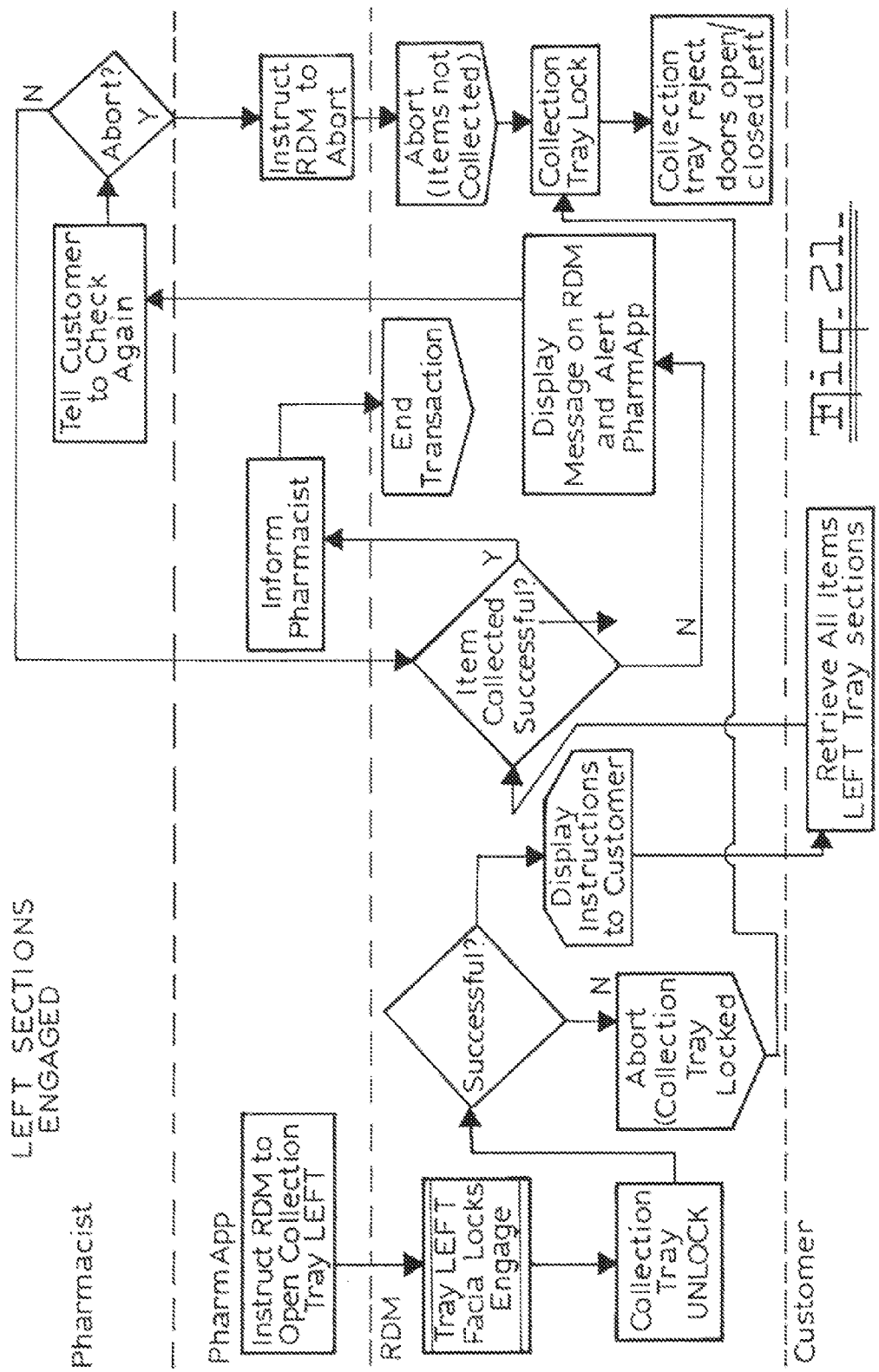
Figure 22:
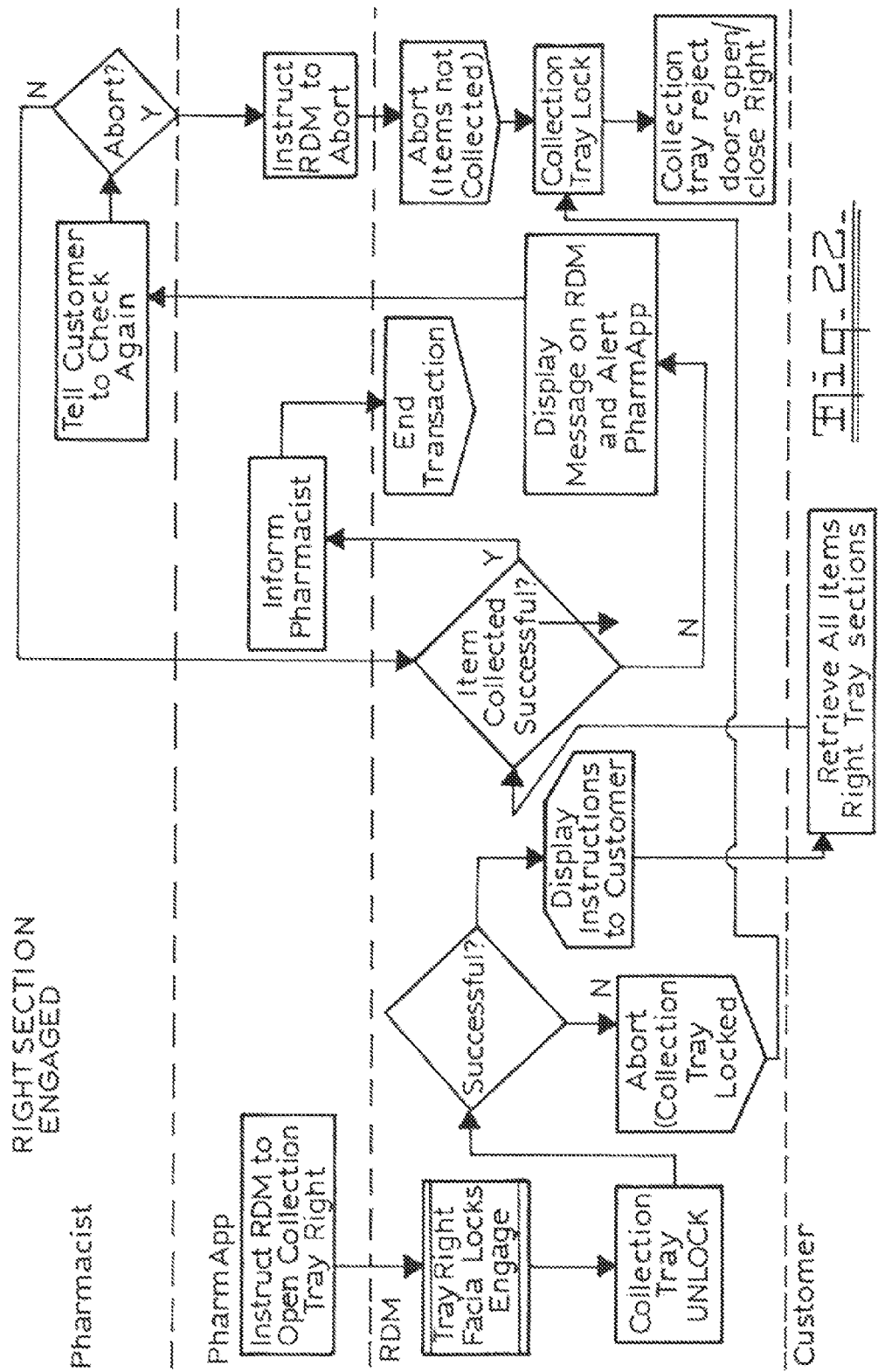

FIGS. 11A and B illustrate the issue tray of the module of FIG. 8;

FIGS. 12A and B illustrate the reject bin of the module of FIG. 8;

FIGS. 13A and B illustrate the product chute of the module of FIG. 8;

FIG. 14 schematically illustrates the hardware components used in the purchaser interface module of the RDM;

FIG. 15 is a schematic diagram of the process overview of the pharmacy dispensing system;

FIG. 16 is a flowchart setting out the script handling process for this preferred pharmacy embodiment;

FIG. 17 is a flow chart illustrating the first phase of the supply of goods sequence;

FIG. 18 is a flow chart illustrating the second phase of the supply of goods sequence;

FIG. 19 illustrates a larger version of the dispenser having two storage cabinets and one purchaser interface module, FIGS. 20A, B C and D illustrates an improved collection tray;

FIG. 21 is a decision diagram showing the operation of the collection tray 20A and 20C FIG. 22 is a decision diagram showing the operation of collection tray 20A and 20D.

Figure 23:
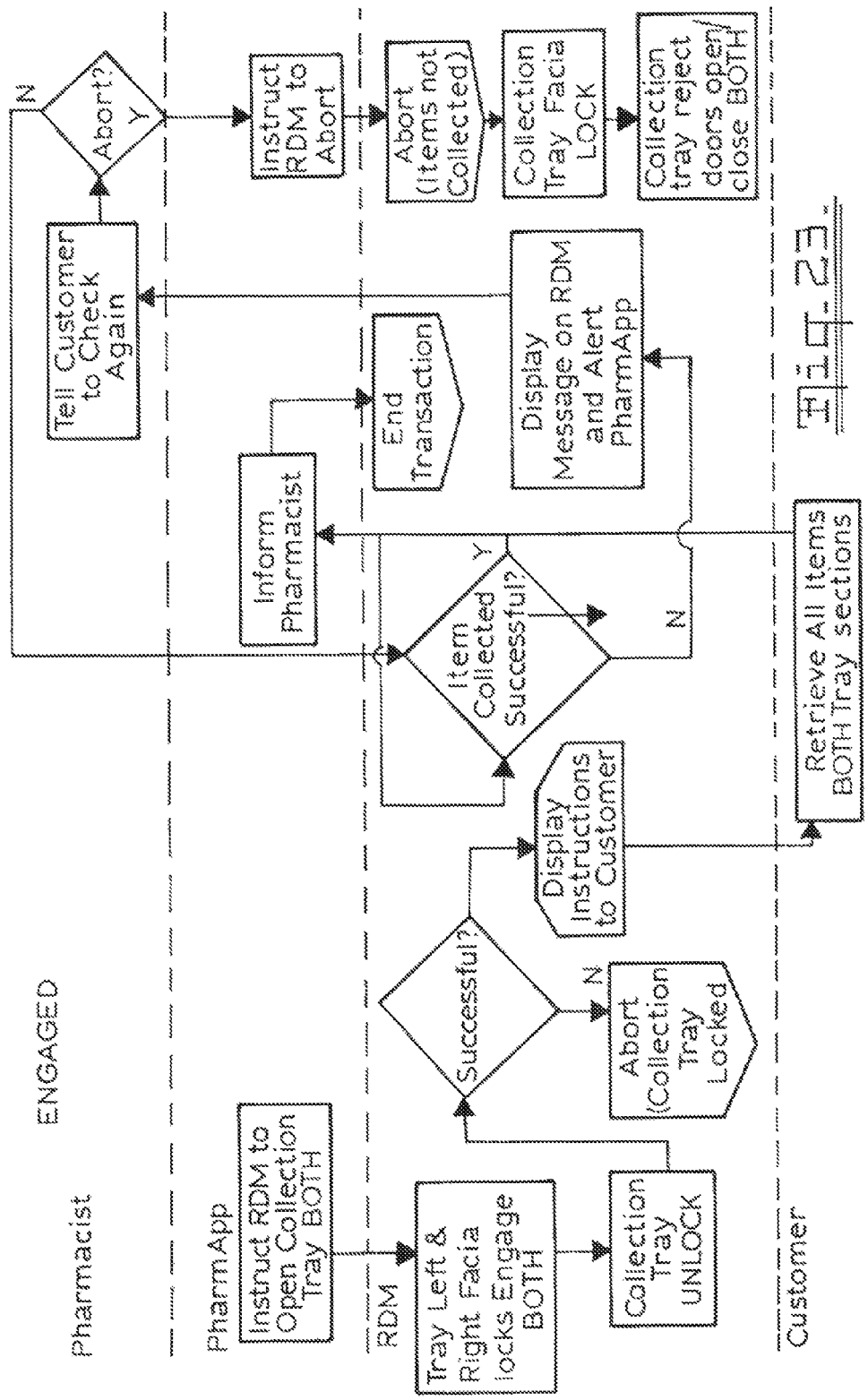

FIG. 23 is a decision diagram showing the operation of collection tray 20A and 20B.

The dispensing machine comprises three main functional modules that can be assembled together in various arrangements based on the requirements of the location in which the machine will be operated.

The modules are Storage Module incorporating the Processing Module, Base Module and Interface module.

Storage Module

The storage module contains the gantry row and column product transport system with magazines of product. The storage module also contains a sub module defined for processing of the items picked for supply to a patient such as; machine identification via barcode scanning or RFID, viewing by camera(s) and inspection by the pharmacist, label printing and application and reject bin access. The processing module may be arranged adjacent to the storage module on either side of the storage module based on which side of the based module the Interface module is situated.

The processing module provides an opening for the gantry arm and pick up unit to traverse between the storage module and the processing module. In normal operation this opening is maintained to ensure that the gantry arm and attached pick up unit can traverse freely and without contacting surrounding enclosure. In the instance where a non pharmacist supervised maintenance routine is required to be performed in the processing module then there is a means provided to move the gantry arm and pick up unit into a specified location in the storage module and via a system controlled mechanism for a closure be moved into place to shut the opening between the processing module and the storage module. This is required to ensure that a technician who may be access the processing module to perform a maintenance task is not able to access restricted items located adjacent to the processing module opening in the storage module tray chutes. Another method to provide this level of restriction to a person accessing the processing module may be via a mechanical linkage between the processing module security door and an internal security flap that moves into place to shut off the opening as the processing module security door is opened. The lever arrangement would ensure that once the processing module security door was fully open the internal security flap is fully closed and locked in position.

Base Module

The base module supports the storage module and contains the machine control system and other peripheral control equipment such as power supply and distribution, uninterrupted power supply unit, pneumatics control system, PLC control system. The base module can be accessed by one or several drawers which can be opened by a qualified person who has identified themselves to the system and has received approval from an authorised person to enable such access.

Base module can be adjusted to ensure it is level and also provide for the module to be secured to the floor or surrounding walls.

Storage module is mounted on top of base module and fixed.

Interface module can be arranged or located on either side of the assembled base and storage module, is able to be adjusted for height and to ensure it is level and then secured to the storage module and to the floor and surrounding walls.

Storage modules can be mounted and arranged on either or both sides of the interface module effectively doubling the capacity of the terminal location.

Between the assembled base and storage module and the interface module a filler panel can be provided to provide some variation in the distance between the assembled base/storage module and then interface module to enable the mounting of various common building materials such as glass, stud framing with fibreboard plasterboard sheet or structural sheet or masonry block wall or solid slab wall to be installed or mounted perpendicularly up to the filler panel effectively providing a physical barrier between the assembled base/storage module and the interface module. This provides the ability to situate the assembled base/storage modules inside a physically secure environment and have the interface module accessible in an adjacent lower security environment. This could be arranged so that the interface module is accessible at the front of an existing retail premises or have the complete terminal located completely inside a secure premises such as a medical clinical or hospital clinic or ward or located so that patients/consumers can access the interface module at any time even when the retail premises is closed to provide after hours service. This is similar to banking ATM foyers that are provided to enable customers to access a private foyer area at the front of an existing bank premises without being able to access the secure main bank area. The interface module can also be orientated to enable the assembled base storage module to be located to the rear of interface module providing the option to only present only the interface module facia to a low security area similar to the way many 'hole in the wall' ATM terminals are arranged. In this arrangement the interface module reject bin would not be able to be accessed from the front of the interface module as per the current embodiment.

Access Control

Authorised Access areas and general access areas of the dispenser are provided. Only suitably authorised persons may access the authorised access areas Pharmacy Only Areas General access areas may be entered without requiring the attendance or supervision of an authorised person but require the notification of the authorised person who is required to access the specific terminal and place it into a relevant operational mode. This routine may be performed by an authorised person who is logged into and able to control the specific terminal requiring access. To enable the technician to be able to access the general access areas.

The base module may be accessed by an qualified person such as an IT technician or PLC engineer, without having to access the storage module or sub modules such as processing module reject bin, interface module reject bin, prescription storage box (if utilised), that can only be accessed by authorised persons such as a pharmacist or pharmacy technician or an authorised person under the remote supervision of an authorised vendor.

Figure 1:
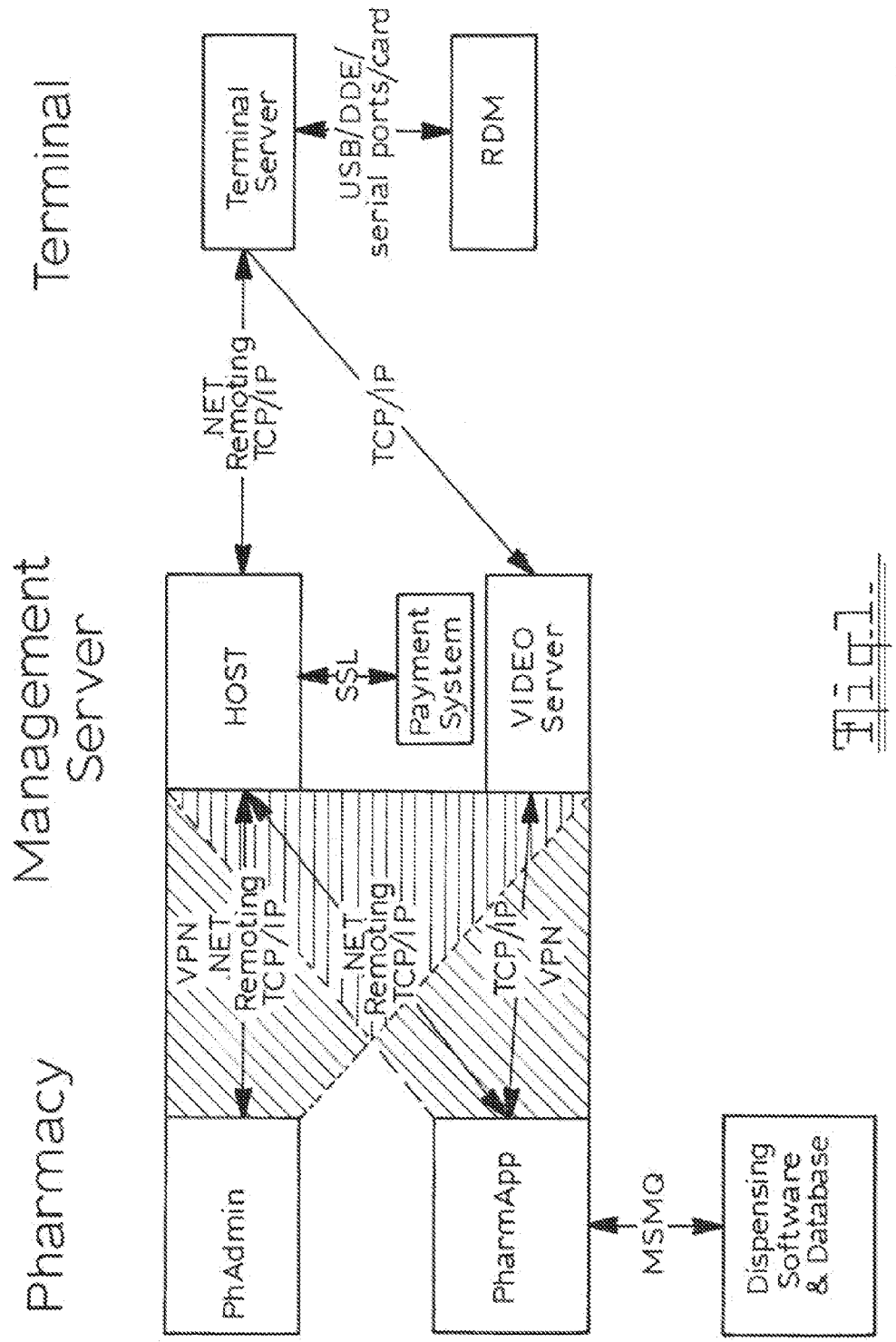
Figure 2:
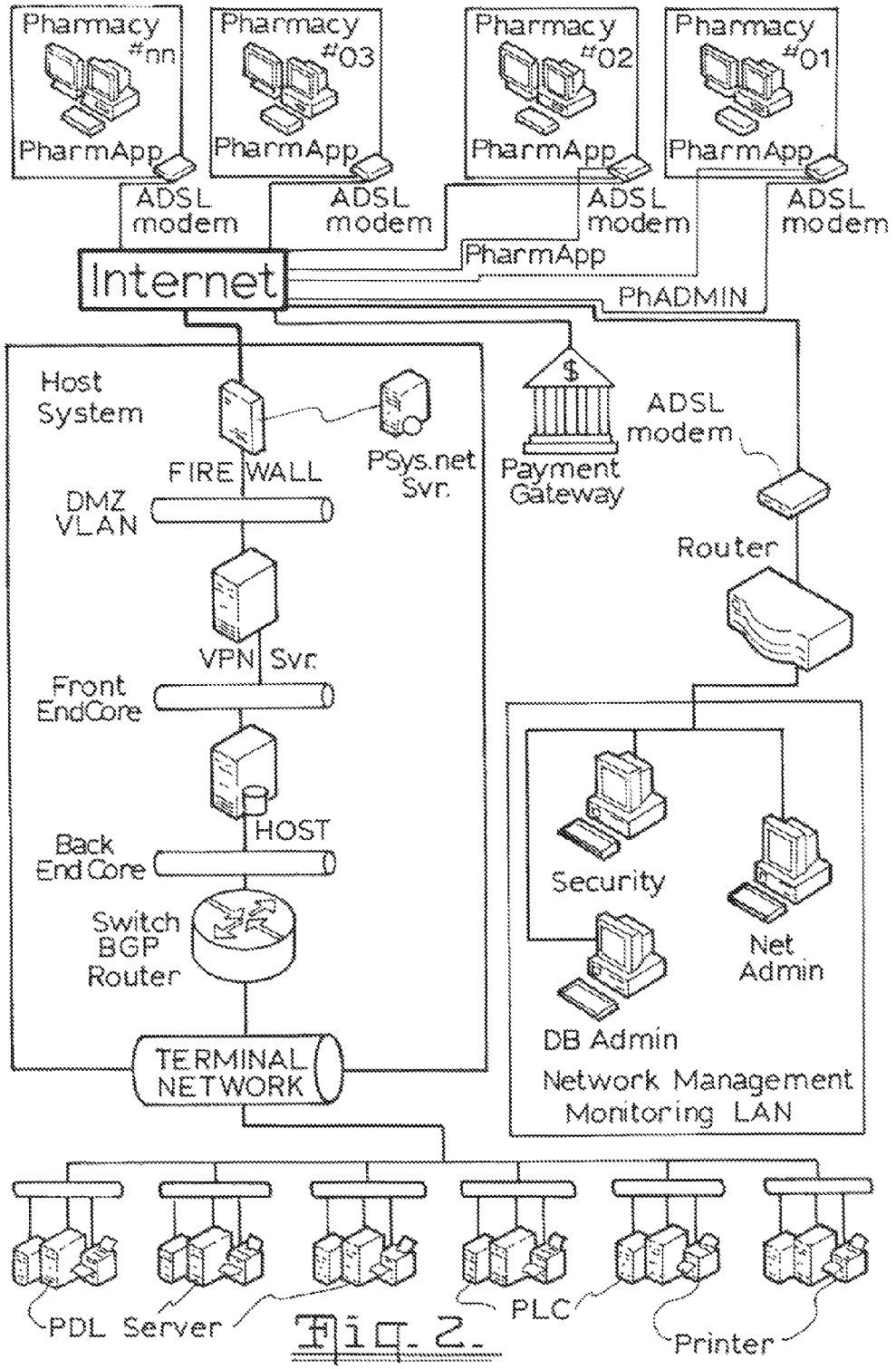
FIG. 2 is a schematic diagram of the communication network for the system of FIG. 1.
Figure 3:
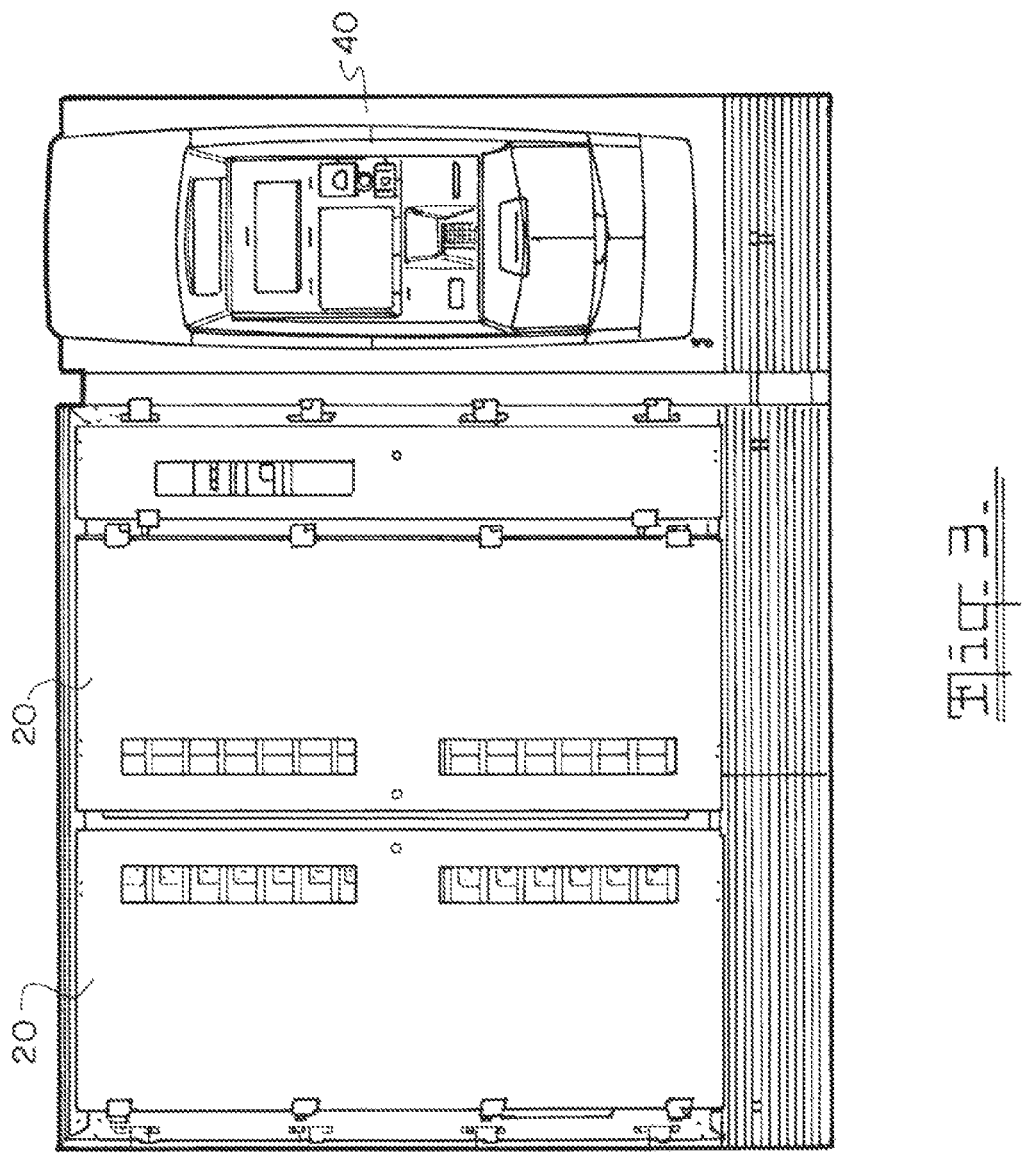
FIG. 3 is a representation of an RDM according to this embodiment.
Figure 4:
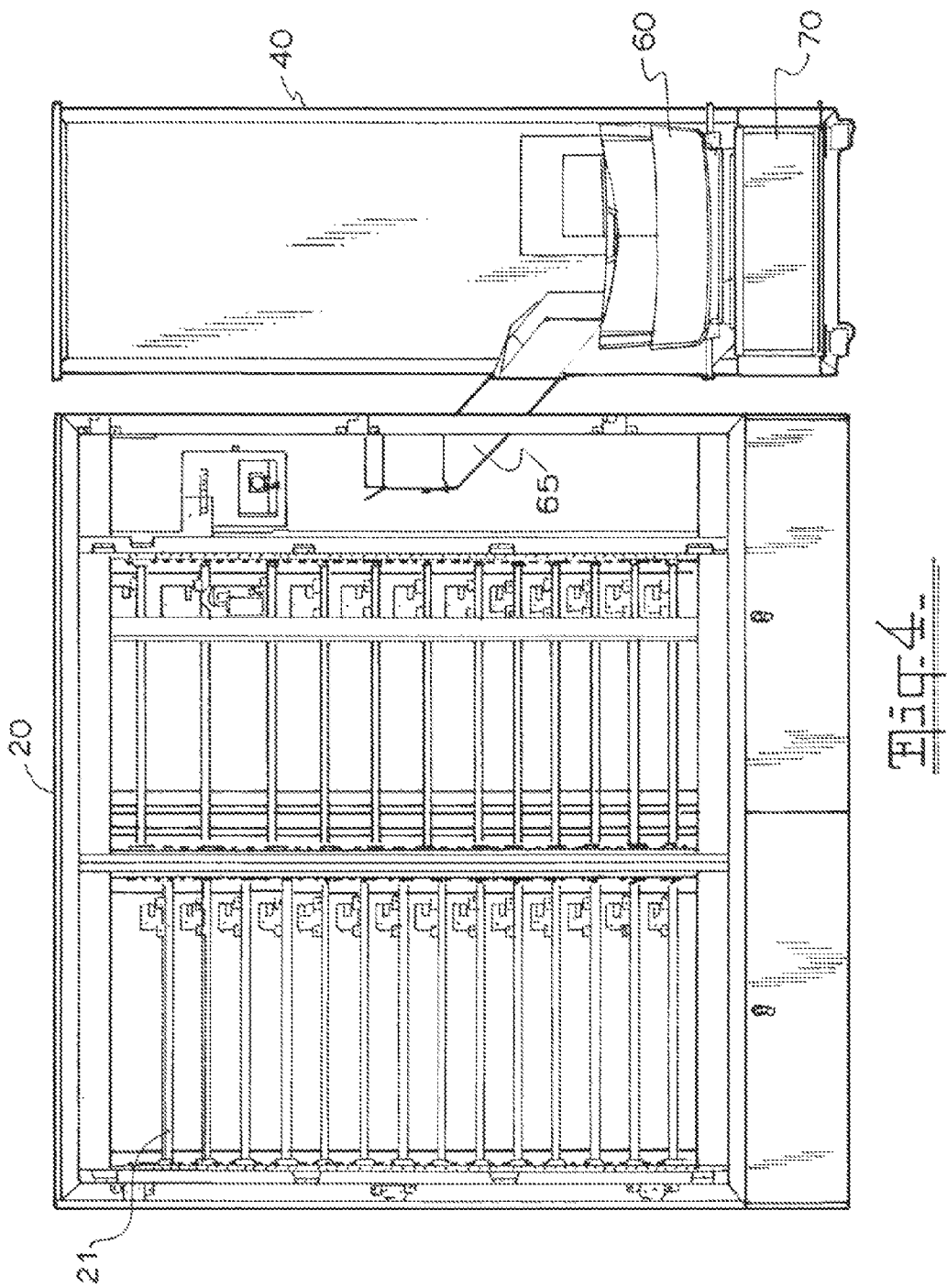
FIG. 4 is schematic front view of the interior of the RDM of FIG. 3.
Figures 5, 6:
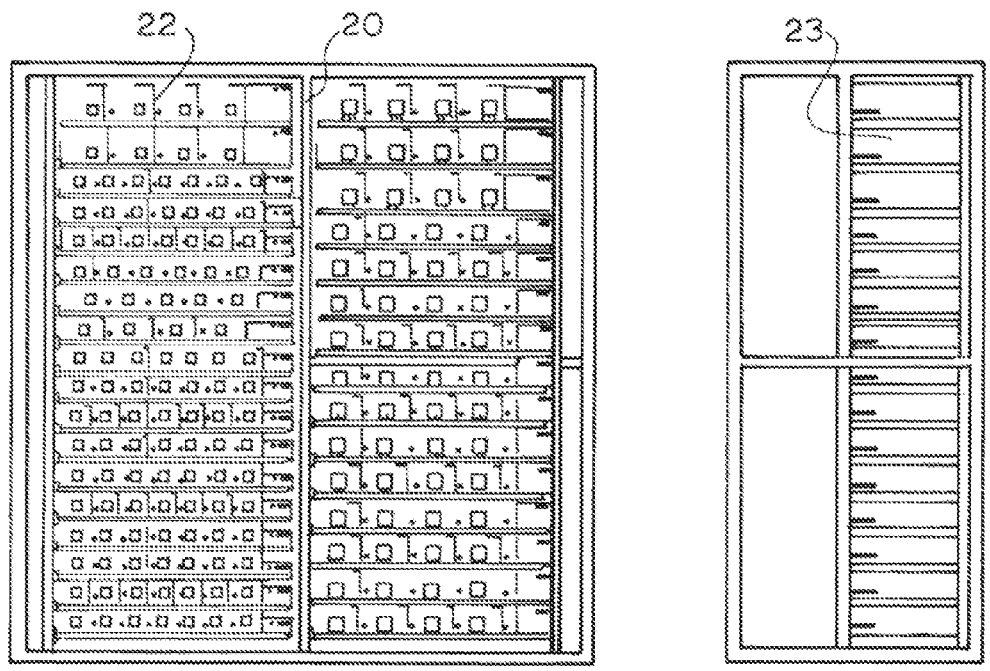
FIG. 5 is a detailed view of a possible shelf layout of the storage unit of the RDM.
FIG. 6 is an end cross section of FIG. 5.

As shown in FIG. 1 the communication and control system is in three sectors namely a host to support a number of pharmacies and a number of remote dispensing machines. The host manages the queuing of RDM calls for a pharmacist and the queuing of pharmacists as they become available for consultation (see FIG. 15). The RDM incorporates arrange of devices and subsystems including a payment system generally indicated as EFTPOS. As shown in FIG. 2 each pharmacist station incorporates a computer station and keyboard and a modem for connection to host computer and its data centre. Each RDM also has an internet modem and also a bank compatible modem for the payment system. Optionally there may be access to the RDM by warehousing and retail management to monitor stocking levels and performance of the system.

Figure 7:
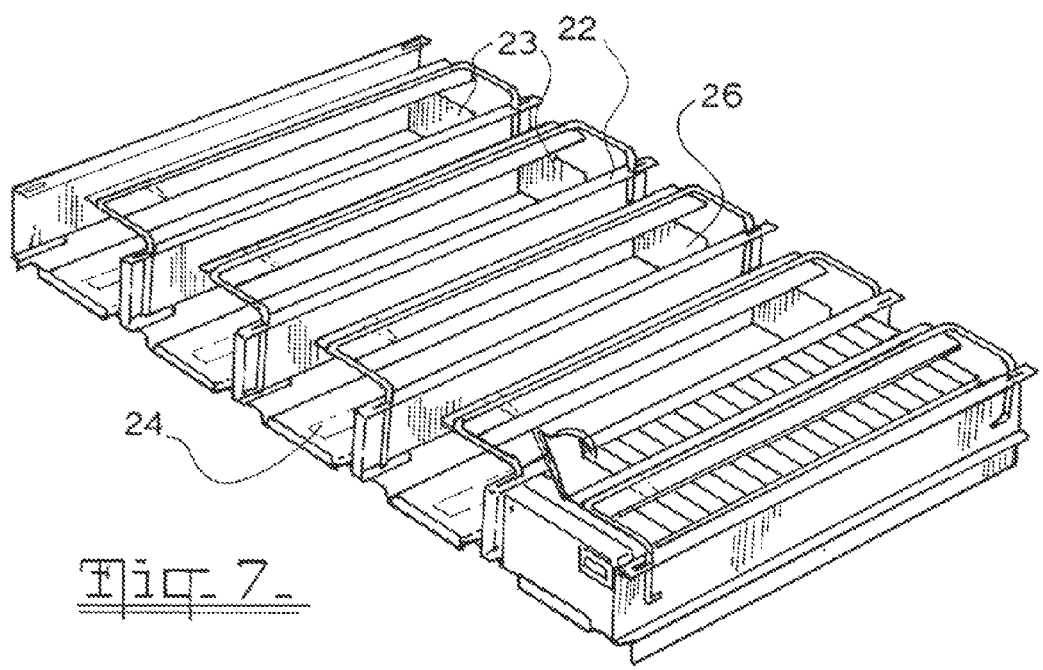
FIG. 7 is a detail of the tray construction for each shelf of the RDM.

The remote dispensing unit as shown in FIGS. 3 to 6 comprises a sealed inventory storage unit 20 and a purchaser interface module 40. The two are linked by electronic cables and the dispensing chute 65. The storage module includes adjustable shelves 21 and which can be fixed at varying heights and spacings. The adjustable side guides 22 to form variable width compartments 23. As shown in FIG. 7 the compartments 23 may include a pressure plate 26 to urge the packs of product forward, over a low friction base 24 to each compartment, toward the forward end. The product packs are packed and stored so that the bar code is readable from the front of the storage unit. When packed the location of each group of packs having the same bar code is stored in the RDM inventory memory.

Product Locations and Tray Setup

The system may include an automatic routine that allows the pick head to follow a present default start position and then track vertically in storage column A until it receives a signal that a tray is located. Once this tray is located the pick system will track horizontally to identify the coordinates of each tray chute location. These coordinates are logged into a database. Once the tray chutes locations are identified and located they are recorded in the terminal systems control memory. This process is repeated for each tray mounted vertically in each column and also for each tray chute divider located horizontally across each tray.

The locations can be changed at any time by physically relocating tray chute locations by an authorised person under supervision of the authorised vendor and then once the routine is completed the system will self check and record the new coordinates of each tray, tray chute divider and record the machine identification or barcode of the item stored in each specific storage location.

The product pickup unit moves in a space in front of the shelves 21 within the storage compartment 20. When a product is selected the pick up unit moves vertically and horizontally to align with the compartment location as stored in the memory. The pick up unit includes a bar code reader to verify that the pack is correct. If it is not correct the pickup unit takes the packet and drops it in the reject bin chute.

The pack may be imaged by multiple cameras and the images shown to pharmacist. Cameras may image and check barcode types to enable machine identification. Or multiple axis barcode scanning array may image all sides of pack to allow the manufacturer's barcode information to be read from any pack side or face.

The pack is picked and taken to an identification area in processing module. If it is acceptable the pharmacist then authorize its move to the label location for label process printing. If barcode identification check fails or the barcode check identifies wrong code then pick head releases item directly to processing module reject bin in processing module or purchaser transaction module Label printing is not always required on every item, rather on items that are required to be supplied either by a Pharmacist only or by prescription. The pharmacist is able to view the printed label and confirm whether the item is authorised for supply to authorised purchaser and placed in the collection tray. If not the item is rejected and the pick system places the item in the chute which leads to the reject bin.

Figure 9:
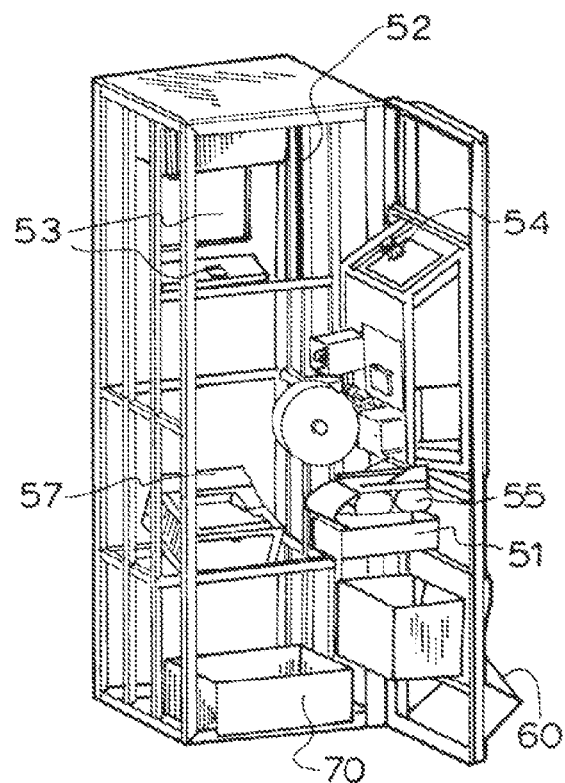
FIG. 9 is an internal view of the module of FIG. 8.
Figure 10:
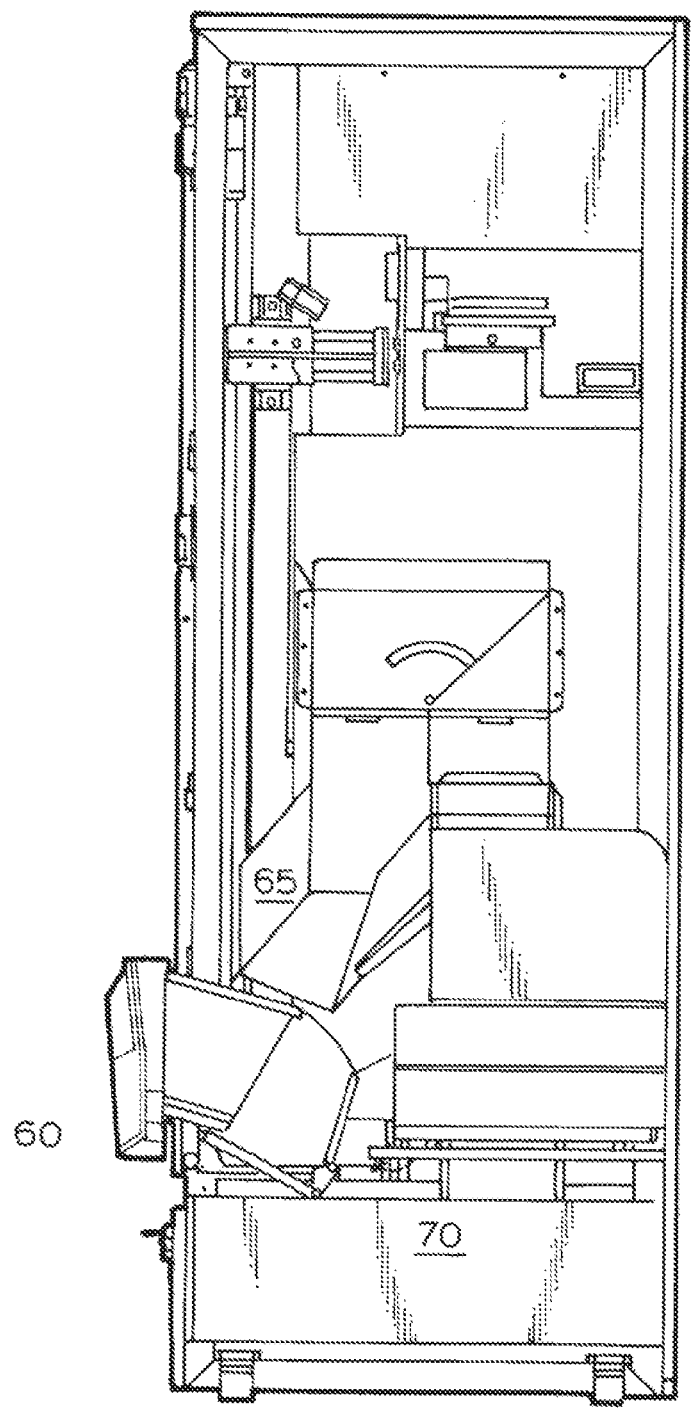
FIG. 10 is an internal end view of the module of FIG. 8.

The purchaser interface module 40 is securely bolted to the storage module 20 as shown in FIGS. 8 to 10 and includes a machine access panel 42 that is shown open in FIG. 9. The main console includes a payment panel such as a credit card or electronics fund transfer panel 43, a health card identification panel or slot 44 which may scan or photograph the card. The console may include a transaction receipt printer 46 and a repeat authorization printer 47. The RDM may be activated by actuating a transaction start key or lifting the handset 48 which connects to the available pharmacist.

The prescription scanner slot 49 allows the prescription to be processed by the script scanner 55 and then stored in the script collection drawer which has restricted access for the pharmacy staff only. If the script collection drawer is not used the script is scanned and placed in the collection tray. Upon viewing of the scanned script image by the vendor the script can be returned to the purchaser by the pharmacist authorizing the unlocking of the collection tray for return to the purchaser or the vendor can authorize the reject clearance of the collection tray securing the script and relocking the collection tray.

A security camera 54 allows the pharmacist to view the purchaser and any identification they may need to produce.

Inside the module 40 is a processor and electronics mounting rack 52 and maintenance peripherals 53 as well as a label printer 57.

Figure 12B:
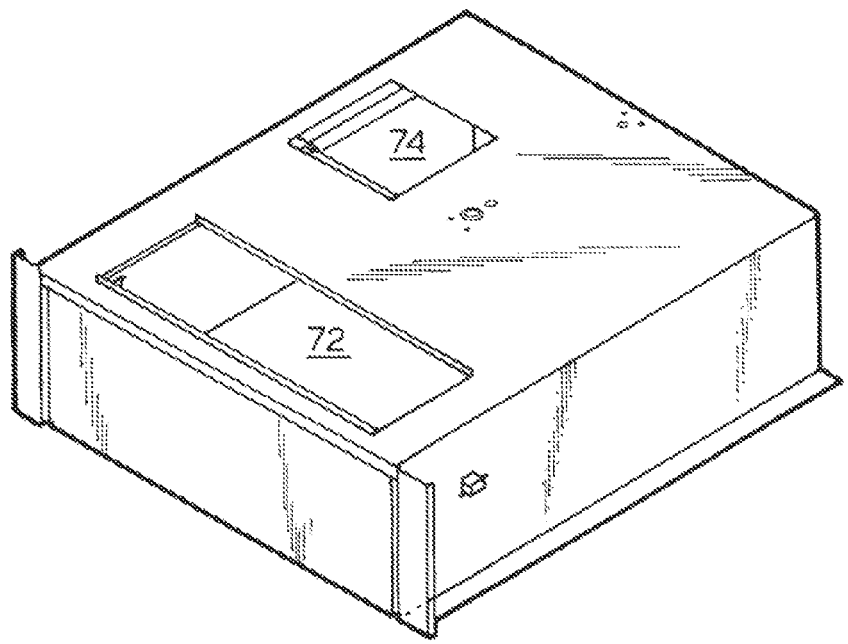
Figure 13B:
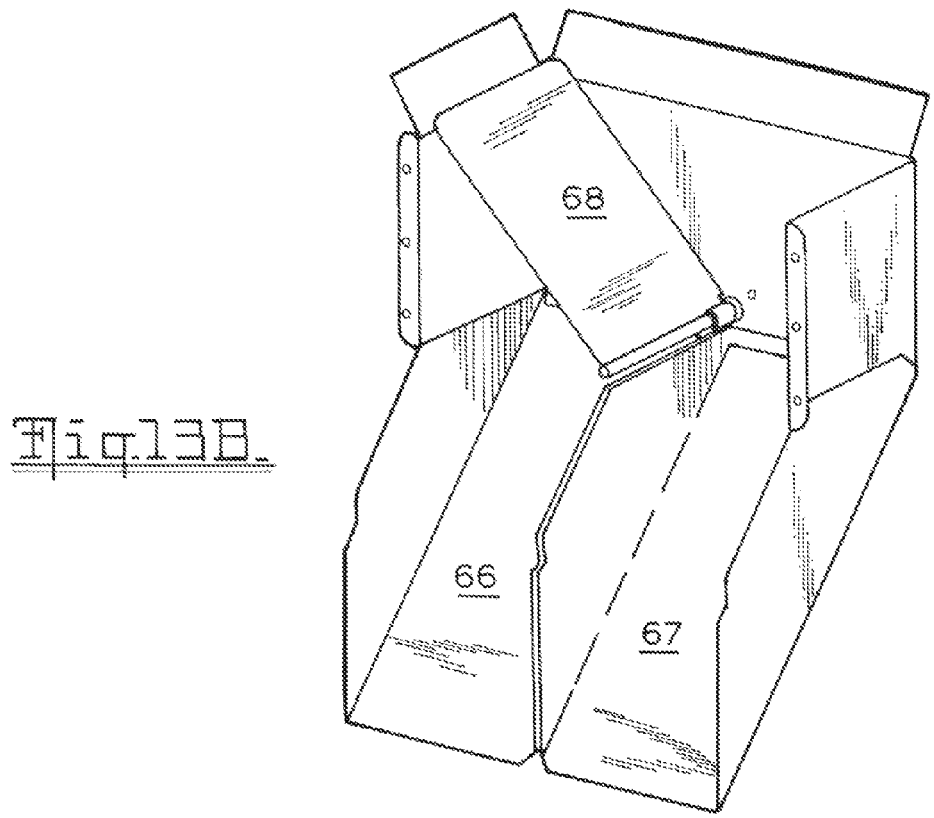

FIGS. 11A and B illustrate the issue tray, which is lockable and pivots so that when unlocked electronically by the pharmacist, it can be tilted forward to allow collection of the dispensed products. The base of the issue tray incorporates a pair of pivoted panels 62 that can be opened by movement of the lever 63, if the transaction is to be aborted after product has been deposited in the issue tray 60. The reject bin 70 shown in FIG. 12 is located below the issue tray and has opening 72 for access from the collection tray 60 and opening 74 which receives rejected product from chute 65, which is shown in detail in FIG. 13. The chute 65 has two channels 66 and 67 which may be covered by deflector plate 68. Channel 66 leads to the issue tray and channel 67 leads to opening 74 in reject bin 70.

When product is verified for sending to the issue tray the deflector 68 is positioned over channel 67 before the pick up unit releases the product. If the product is to be rejected the deflector 68 is switched to cover the channel 66 so that when released from the pick up unit the product slides into the bin 70.

In an alternate arrangement two reject bins are used. The second bin is preferably located in the storage unit 20 below the chute 65 so that for transactions or parts of transactions aborted prior to the product being sent to the collection tray the documents and product can go straight to the rejection bin. In this second alternative two chutes replace chute 65 and deflector plate 68. One leads to the second reject bin and the other to collection tray 60. The reject bin 70 below the collection tray 60 is then reserved for transactions aborted after the product and documentation are sent to the collection tray. Another arrangement is for the chute 67 to be replaced by a reject bin in the processing module that enables the deflector 68 to be switched to cover the channel 66 so that when released from the pick up unit the product slides into the reject bin located in the processing module. This reject bin would incorporate a lockable lid to ensure that only an authorised person under the supervision of the authorised vendor is able to access the reject bin to clear rejected items.

FIG. 14 illustrates the hardware components used in the RDM.

The purchaser initiates a transaction by actuating call button 100 and may also be provided with an LCD panel 101 which can display transaction instructions and if desired, provide visual images of the pharmacist. The access keypad 102 and the telephone 48 (or a microphone and speaker unit) provide for clear communication to the pharmacist. The EFT-POS unit will include a card reader 43A and a keypad 43B.

As can be seen a number of printers are required and up to 4 video or still cameras are provided for the pharmacist to view the product 44A, the purchasers health card 44B and two cameras 54 to view the customer from different orientations.

The system preferably provides for multiple authorised Vendors including Pharmacy Technician as well as the pharmacist.

A pharmacy technician may commence the transaction, but the pharmacist may complete a clinical check (check prescription, patient history, patient responses) hand back to Pharmacy Technician for processing, then hand back to pharmacist for counselling and release of product to patient via unlocking collection tray. The pharmacist is able to supervise all processes and information that the Pharmacy Technician undertakes should this review be required to confirm transaction details or information provided from the authorised purchaser in order to adequately confirm information to follow safe dispensing practices.

The processing of a purchase is shown in FIGS. 15 and 16. Queuing programs connect an available pharmacist to the next in queue RDM terminal. The host computer communicates with a pharmacy support software system that is used in each pharmacy. This is done through a host administration system that includes modules for billing, data storage, certification management, and auditing. The host computer also communicates with the RDM terminal and each pharmacy and provides the data and video links between the pharmacy and the RDM terminal. The voice link is preferably direct between pharmacy and the RDM terminal but an alternative is to have the voice link communicate via the host computer and then communicate to the pharmacy.

The pharmacist logs into system when available in the dispensary. The system switches the dispensing terminal to available mode, activating the terminal call button and changing information screens to advise that a pharmacist is available. The system then waits for the customer to activate the call button.

The pharmacist can log out when leaving the dispensary. The system switches the terminal to unavailable mode, deactivating the terminal call button and changing the information screens to notify customers at the terminal that a pharmacist is not available.

The prescription is inserted in a secure script tray after which the script is scanned and the image viewed by the pharmacist.

The customer presses call button, the system notifies the pharmacist in the dispensary and the pharmacist accepts the call request. The customer is provided a call receipt which provides transaction number and relevant pharmacist contact support information.

Upon confirmation of a transaction request from a terminal by an authorised vendor the terminal prints a contact receipt or coupon for the purchaser. This provides information about the authorised vendor, their name, location, contact details and any other information that may be required based on specific territory regulations where they are registered to practice, the location of the terminal that the purchaser is using and contact numbers or details to enable them to contact the authorised vendor and a specific transaction identifier to identify the specific transaction event to the authorised vendor should they require support if the transaction fails or is unable to be completed. This may eventuate due to machine failure, loss of communications between the authorised vendor and the management server, loss of communications between the management server and the terminal, loss of communications between the authorised vendor and the purchaser.

The pharmacist welcomes customer and consults with customer as to the nature of the service. At the request of the pharmacist, the script scan lid is unlocked, customer then inserts scripts which are scanned and viewed by pharmacist in dispensary. The pharmacist can also view and/or store images of identification cards such as Medicare, Drivers Licence and health Insurance cards. In the case of an electronic prescription the customer inserts script coupon (eScript), and the system scans the coupon, reads unique ID number or bar code and notifies the eScript provider of the request. The eScript is sent to the authorised dispenser location by the provider or the coupon number is matched to the relevant eScript that has been provided to the dispenser by the prescriber on request of customer. An eScript may also be scanned by alternative means such as a non contact visual or laser scanner to enable indentification of the eScript identification number.

The pharmacist may open the script input slot or enable script scanning (script is scanned and placed in collection tray)

The dispenser may provide a section of the collection tray that is only for the scripts to be stored in.

The prescription input slot is located adjacent and above the collection tray assembly. This arrangement allows for each prescription or paper order to be fed through the scanned and then directed into the central storage area of the collection tray. The authorised vendor may elect to unlock and open the complete collection tray or unlock only the central section of the collection tray so the authorised purchaser to collect the prescriptions. This may be required in circumstance's where regulations do not allow for the item prescribed to be supplied via a remote dispensing terminal, or where the item is not available from the specific terminal and the authorised purchaser is not willing to receive the item via another supply method such as post or courier, and therefore requires the prescription to be returned to them. In some territories some medications or products are considered to be controlled items and can only be supplied to authorised persons who present in person to the pharmacy. Another exception is where the prescription needs to be returned to the authorised person, for the authorised person to physically sign or imprint the prescription, prior to the completion of the transaction and prior to supply of items.

Where the script needs to be returned to the customer the pharmacist will open collection tray (pre product supply to collection tray)

The collection tray can be divided into specific sections to enable only necessary sections to be opened subject to the authorisation of the authorised vendor to accommodate specific situations or that meet specific transaction requirements or transaction stages. If required by the authorised vendor the central section of the collection tray may be unlocked to only allow the prescription collection area to be opened and accessed by the authorised person. Unlocking of the prescription collection area separately to the complete collection tray ensures only the central collection tray area would rotate about a pivot enabling access to the secure area containing the scanned prescriptions. If the central collection tray section remained locked while the main collection tray locks were unlocked this would enable the whole collection assembly to be opened and provide the authorised person access to all of the collection tray areas containing prescriptions and or authorised supply items. Each area of the collection tray would be able to have items contained rejected by actuation of the collection tray reject mechanism. The dual collection tray provides greater flexibility. In a large system as shown in FIG. 19 items from one storage cabinet can be passed to one collection unit and items from the other storage to the second collection unit. The two storage sections may be used for different categories of pharmaceuticals or drugs requiring different security regimes. One storage module may be refrigerated so that one collection tray unit will be for the collection of those products. Alternatively paper documents such as information sheets or repeat prescriptions may be placed in one unit separate from the dispensed items.

If the pharmacist is able to fill the request without prescription or with a prescription from the inventory in the RDM terminal, the transaction proceeds and the script is passed to the script storage tray 51.

The pharmacist switches to the dispensing application system to complete a patient history review, clinical checks, and asks the customer questions as required and then prepares dispensing information label, CMI's and prescription repeats. If the script cannot be filled either by supply from the RDM terminal or from the dispensary, the authorised vendor can discuss with the authorised person what options may be available to supply the product to the authorised person by other means available. These may be via post, courier or by the authorised person collecting the restricted item from the authorised vendors premises.

In some cases the pharmacist will want to place transactions on hold. In certain circumstances the authorised vendor will require discussion with the prescriber or patient carer, guardian etc., and once discussion has been undertaken and the issue resolved to the satisfaction of the authorised vendor then the transaction can be recommenced when patient represents to the terminal for the transaction to be completed.

Once the authorised vendor has completed any administration on the authorised persons request the session can be aborted or closed by standard operating procedures or administration processes and the script tray or collection tray is opened and the purchaser can remove the script.

Dispensing information is then completed by the terminal control system while the pharmacist monitors the printing of documents, the picking of the product, views the picked product, authorises label printing, views printed label and authorises product to be placed in secure collection tray.

The sequence of events within the RDM terminal is set out in FIGS. 16-18. The product selected by the pharmacist is picked by the control mechanism sending the pick arm to the location (row and column) stored in memory. The scanner on the pick arm scans the barcode on the product at that location and verifies that the bar code is the correct one. The product is then picked and conveyed to the label printer where it is positioned at the print head. After each line of print is completed the pack is moved up one line for the next line of print or the print head moves one line while the pack remains in a fixed location. When all lines are printed the pick arm conveys the pack to the camera location so that the pharmacist can view the pack barcode and the printed label. If the pack is approved the product is placed in the issue tray. During this process the system display indicates the stage in the process as shown in FIG. 17. Alternatively the label may be printed and then applied to the pack.

FIG. 19 illustrates a dispenser with two inventory storage modules 20 and one transaction module 40. Each inventory storage 20 includes a processing module 110 which includes a bar code scanner, video and/or still image camera and label printer. In operation the product holder carries a selected product to the processing module 110 for the preparation of the product prior to dispensing. The video or still image camera allows the pharmacist to view the labelled product to ensure everything is correct.

A holding unit 120 allows the product to be held adjacent the processing module should the pharmacist decide to delay sending the product to the collection tray via the chute 65. When the Pharmacist finally decides the fate of the product in the holding tray 120 it can be dispensed to chute 65 or into the reject bin 70 located in the storage module 20 below the processing module 110.

Figure 11B:
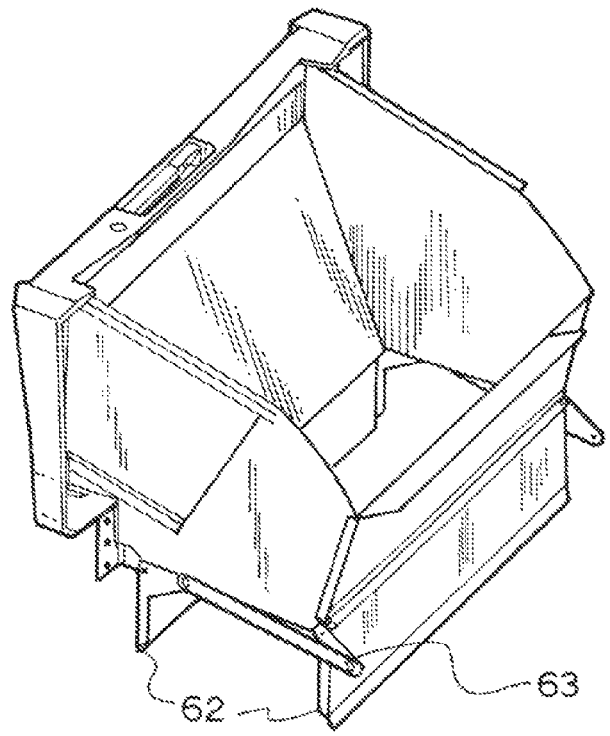
Figure 20:
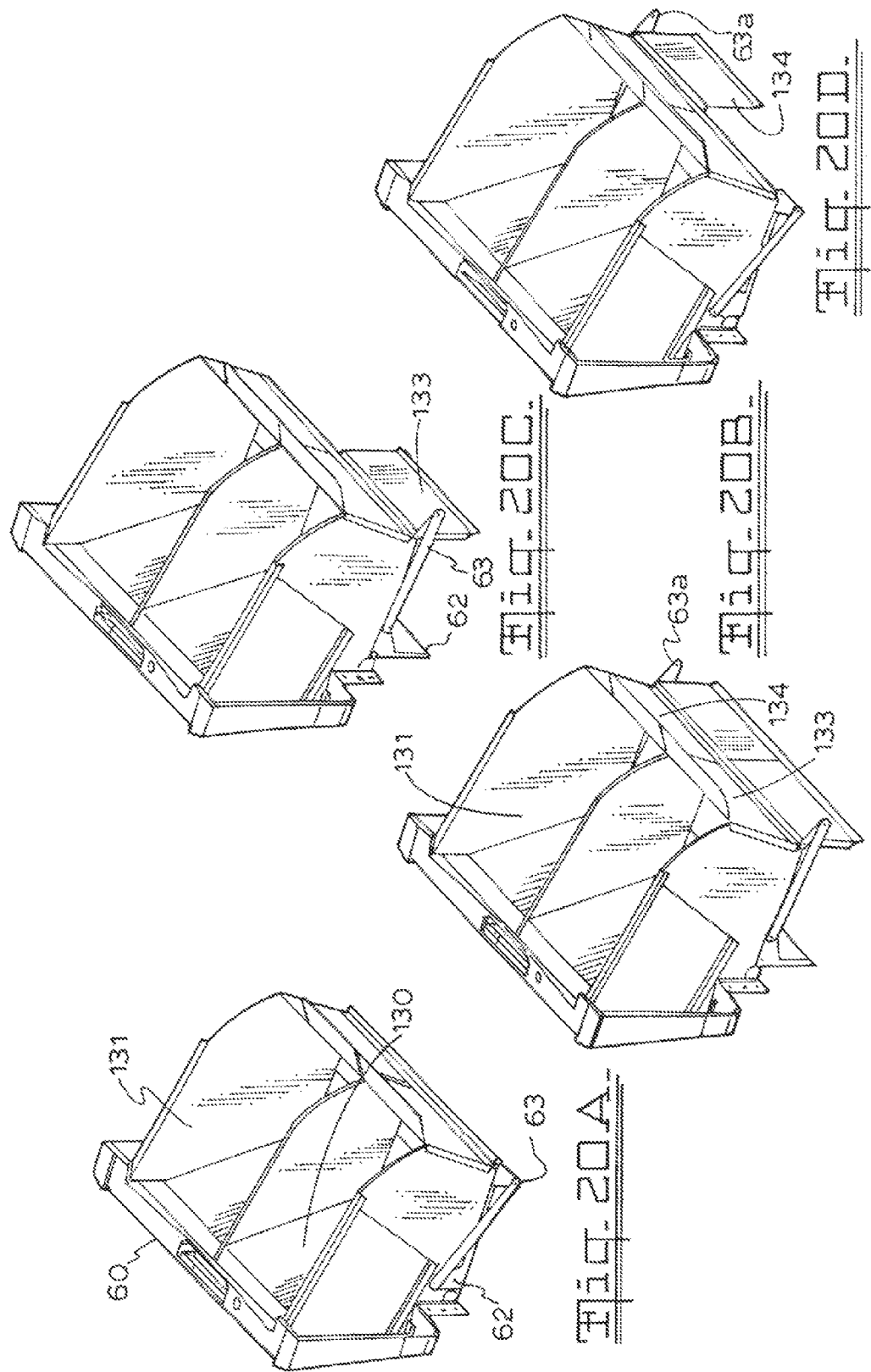

As shown in FIG. 20 the improved collection tray is overall the same as shown in FIG. 11 but the actual holding units 130 and 131 are detachable from the front facia/handle 136 of the tray 60 so that unit 130 or 131 can be pulled out independently of each other. Similarly the rear gates 133 and 134 for units 130 and 131 respectively can be independently actuated.

FIG. 21 illustrates the sequence of operation of the left unit 130. If the tray is unlocked the fascia 136 engages unit 130 and can be pulled out by the customer to retrieve the items in unit 130. If the items are not collected the items in unit 130 can be dropped into the reject bin 70 by opening gate 133 as shown in FIG. 20C. FIG. 22 illustrates the sequence of operation of the right unit 131. If the tray is unlocked the fascia 136 engages unit 131 and can be pulled out by the customer to retrieve the items in unit 131. If the items are not collected the items in unit 131 can be dropped into the reject bin 70 by opening gate 134 as shown in FIG. 20D. FIG. 23 illustrates the sequence of operation of both units 130 and 131 simultaneously. If the tray is unlocked the fascia 136 engages both units 130 and 131 and can be pulled out by the customer to retrieve the items in both units 130 and 131. If the items are not collected, the items in units 130 and 131 are dropped into the reject bin 70 by opening gates 133 and 134 as shown in FIG. 20B.

In the circumstance that a particular product is known or suspected to be unsuitable for supply to an authorised purchaser then the particular row and column location in the inventory storage area, the authorised vendor may restrict supply of items from this or a number of other discrete row and column locations. The reasons for restriction may be numerous but may be for reasons such as damage to item by the product selection device, an item or batch of items has reached the expiry date or is likely to expire within a designated period and should be removed from the terminal as the items may not be consumed in full before the expiry date is reached. These unsuitable items may be placed in a reject hopper located within the inventory storage to be collected at the next maintenance visit to the remote dispenser.

The pharmacist may actuate the reject system at any point in the transaction for whatever reason the pharmacist decides that the items in the collection tray should not be supplied to the authorised purchaser. It may be that the authorised purchaser has vacated the terminal or it has become apparent to the pharmacist that the authorised purchaser is in fact not the authorised purchaser or that based on their response to questions regard the authorised purchaser medical history that the item(s) supplied to the collection tray are not suitable and may cause harm if supplied to the authorised purchaser.

When the pharmacist is satisfied all items have been processed correctly, payment is completed by the customer via debit or credit or on pharmacy account. Then the receipt and repeat documents are printed and issued. Once payment is completed, the pharmacist authorises the collection tray to be unlocked and instructs customer to collect items. The pharmacist can check off supplied items with customer and complete counselling with the customer. The pharmacist closes the transaction, the collection tray is cleared, the system status is checked and then the system goes back into wait mode for next customer.

A barcode scan is not always required for the item to be enabled to be picked. The use of a camera on the pick unit enables the pharmacist to view the product ready to be picked and enable the pharmacist to authorise the picking of the item. Other identification methods may be used to aid the authorised person in confirming the product ready to be picked in the specified location is correct and able to be picked. This may be via machine vision matching, RFID, or new forms of 2D barcode.

A further development enables multiple views of the picked item to be displayed to the authorised vendor enabling them to view all sides of the picked item providing a means to ensure that the correct product and information contained on the item pack such as batch numbers, product expiry dates, product dosage or dose strength or medication type.

The item once picked is taken to the viewing location where cameras are positioned to enable each face or the product to be viewed while the item is held by the picking unit. The face adjacent to the picking unit is viewed and its face imaged prior to picking and then presented in the authorised vendor software in the correct arrangement as per the actual item. Other techniques to support the identification of the item may be employed to provide accurate information to the authorised vendor; such as via optical character recognition, machine vision, barcode scanning, RFID tags or holograms while the item is in the viewing area. This area may also be shielded from other items to ensure accurate reading, viewing or scanning of the various identification details contained on or within the item packaging. These additional identification processes provide detailed and accurate data to the authorised vendor either by presentation of the data to the authorised vendor for approval or the checking and review of the identification information by automatic decision support databases or algorithms that would warn the authorised vendor that the item selected is not correct or is not suitable for supply and should be rejected.

Several variations of the process can be performed by the pharmacist to provide authorised purchaser access to the product items processed and placed in the collection tray. The pharmacist may elect to unlock the collection tray and provide access to the processed items in the collection tray after each product item or group of items including printed items are processed to the collection tray.

The pharmacist may also elect to keep the collection tray locked until all items and printed matter are processed and placed in the collection tray. Upon the processing of all items the pharmacist can then unlock the collection tray and have the authorised purchaser collect all items.

The pharmacist need not be involved in all aspects of the process as an assistant or pharmacy technician can carry out many of the steps until the final sign off for authorization by pharmacist. In some territories the authorized vendor may not need to be directly involved in the transaction but present to supervise the authorized person undertaking the transaction under the supervision of the authorized vendor.

As can be seen in FIGS. 17 and 18 there are check points at each step in the sequence which, if negative, result in the session being aborted and the product being placed in the reject bin.

Restocking

An authorised vendor supervises the restocking of the dispenser by placing the remote terminal into a specific mode enabling an authorised person to attend the remote terminal and access the storage module.

Upon completion of the restocking routine the authorised person performing the restocking routine will close the security doors of the storage module and the processing module and will inform the terminal control system that restocking is complete. If the control system receives the correct states form the control sensors and safety system then the pick system will perform a check routine of the storage locations for each product. This routine will compare the stored and recorded locations for each tray chute divider and update the database and also store the identified barcode number or machine identifier (RFID) of the product located in each specific storage chute location.

If a product is identified in a specific location that does not match that stored in the terminal control system for that tray chute location then the authorised person is notified and the terminal control system will revert to the previous restocking state to enable the authorised person to access the storage module column and undertake corrective action. Only one storage door may be opened at a time so that one must be shut for the other to be opened.

From the above description it can be seen that this invention provides a unique and safe means of remote issue of restricted goods such as pharmaceuticals. Those skilled in the art will realize that this invention can be implemented in a variety of embodiments without departing from the core teachings of this invention.

The invention claimed is:

1. A method of dispensing restricted products from an authorized vendor to an approved purchaser which includes the steps of
    a) providing a dispenser containing an inventory of restricted goods
    b) providing an audio and data communication link from the dispenser to the authorized vendor
    c) providing means in the dispenser to enable the vendor to verify the purchaser's status as an approved purchaser
    d) providing an inventory system that includes product storage in rows and columns and a product identification system that identifies the location of each product by its row and column
    e) providing a product selection device that enables verification that the product selected is correct and holds and carries the product from its storage location to one or more of a printing location, viewing location and issue tray all located within the dispenser
    f) providing visual viewing means for the vendor to view the product before it is placed in the collection tray
    g) providing a payment transaction system in the dispenser to verify payment for the product
    h) providing at least two collection trays in the dispenser that are locked until the vendor releases the product to the purchaser and which can be accessed independently
    i) providing at least one reject hopper to collect items not approved for collection
    j) the dispenser including a reject system that securely removes product to a reject hopper at any time after the product is held by the product selection device but prior to the vendor releasing the product from the collection tray.

2. A method as claimed in claim 1 which also includes controls actuatable by the vendor to independently lock or release each collection tray and to allow items in either collection tray to be released to a reject hopper.

3. A dispenser for dispensing restricted goods by an authorized vendor to an approved purchaser which includes:
    a) a cabinet containing an inventory storage system, a purchaser transaction module, a reject system and a control system
    b) said inventory storage system includes product storage in rows and columns
    c) said purchaser transaction module including an audio communication link from the dispenser to the authorized vendor, a payment transaction system in the dispenser to verify payment for the product, at least two independently accessible collection trays in the dispenser that are locked until the vendor releases the product to the purchaser and at least one reject hopper to collect items not approved for collection
    d) said reject system securely removes product to a reject hopper at any time after the product is held by the product selection device but prior to the vendor releasing the product from the collection tray
    e) said control system including
        i) an identification device to enable the vendor to verify the purchaser's status as an approved purchaser
        ii) a product identification system that stores the location of each product by its row and column
        iii) a product selection device that enables verification that the product selected is correct and holds and carries the product from its storage location to one or more of a printing location, viewing location and issue tray all located within the dispenser
        iv) a reject key to enable the vendor to actuate the reject system
        v) a release key to unlock the collection tray.

4. A dispenser as claimed in claim 3 which includes two inventory storage systems on either side of the purchaser transaction module.

5. A dispenser as claimed in claim 3 which includes controls actuatable by the vendor to independently lock or release each collection tray and to allow items in either collection tray to be released to a reject hopper.

6. A method of dispensing pharmaceuticals at a location remote from the pharmacist which includes the steps of
  a) providing a dispenser containing an inventory of pharmaceutical products
  b) providing an audio and data communication link from the dispenser to the pharmacist
  c) providing a scanner and video camera in the dispenser to enable the pharmacist to verify the purchaser's status as an approved purchaser
  d) providing an inventory system that includes pharmaceutical product storage in rows and columns and a product identification system that identifies the location of each product by its row and column
  e) providing a product selection device that includes a bar code scanner and which holds and carries the product from its storage location to one or more of a printing location, camera viewing location, reject bin or issue tray all located within the dispenser
  f) providing camera viewing means for the pharmacist to view the product before it is placed in the issue tray
  g) providing a payment transaction system in the dispenser to verify payment for the product
  h) providing at least two collection trays in the dispenser that are locked until the vendor releases the product to the purchaser and which can be accessed independently
  i) providing at least one reject hopper to collect items not approved for collection
  j) the dispenser including a reject system that securely removes product to a reject hopper at any time after the product is held by the product selection device but prior to the vendor releasing the product from the collection tray.

\* \* \* \* \*